US009082319B2

(12) United States Patent
Shimada et al.

(10) Patent No.: US 9,082,319 B2
(45) Date of Patent: Jul. 14, 2015

(54) METHOD, APPARATUS, AND SYSTEM FOR COMPUTER-AIDED TRACKING, NAVIGATION AND MOTION TEACHING

(75) Inventors: Kenji Shimada, Pittsburgh, PA (US); Emily M. Geist, Lewisburg, PA (US)

(73) Assignee: Carnegie Mellon University, Pittsburgh, PA (US)

(*) Notice: Subject to any disclaimer, the term of this patent is extended or adjusted under 35 U.S.C. 154(b) by 1809 days.

(21) Appl. No.: 12/223,230

(22) PCT Filed: Jan. 24, 2007

(86) PCT No.: PCT/US2007/001897
§ 371 (c)(1),
(2), (4) Date: Aug. 10, 2010

(87) PCT Pub. No.: WO2007/087351
PCT Pub. Date: Aug. 2, 2007

(65) Prior Publication Data
US 2010/0299101 A1   Nov. 25, 2010

Related U.S. Application Data

(60) Provisional application No. 60/761,702, filed on Jan. 24, 2006.

(51) Int. Cl.
*G01C 9/00* (2006.01)
*G09B 23/28* (2006.01)
*A61B 19/00* (2006.01)

(52) U.S. Cl.
CPC .............. *G09B 23/28* (2013.01); *A61B 19/22* (2013.01); *A61B 19/52* (2013.01);
(Continued)

(58) Field of Classification Search
CPC ................................ A61B 19/22; G06F 3/011
USPC ...................... 702/127, 150–154, 92, 94, 155
See application file for complete search history.

(56) References Cited

U.S. PATENT DOCUMENTS 4,482,968 A * 11/1984 Inaba et al. ............... 318/568.22
5,251,127 A * 10/1993 Raab ............................. 606/130
(Continued)

FOREIGN PATENT DOCUMENTS

| EP | 0959444 | 11/1999 |
|---|---|---|
| WO | WO03023737 | 3/2003 |
| WO | WO2004030559 | 4/2004 |

OTHER PUBLICATIONS

"PCT Notification Concerning Transmittal of International Preliminary Report on Patentability", dated Aug. 7, 2008, for Application No. PCT/US2007/001897.
(Continued)

*Primary Examiner* — Janet Suglo
*Assistant Examiner* — Yaritza H Perez Bermudez
(74) *Attorney, Agent, or Firm* — Downs Rachlin Martin PLLC

(57) ABSTRACT

Methods, apparatuses, and systems for computer-aided tracking, navigation, and motion tracking. In one embodiment, a system for determining a spatial position, including a tracking device and a processor. The tracking devices has a working end, a reference end, a plurality of links connecting the working end to the reference end, wherein each link has at least one degree of freedom relative to an adjacent link, and a plurality of sensors measuring the orientation of the links in a plurality of degrees of freedom, wherein X is a minimum number of degrees of freedom about which information is required to define the spatial position. The processor receives information from the sensors and determine the spatial position of the working end of the tracking device relative to the reference end of the tracking device based on information from the sensors measuring Y degrees of freedom, wherein Y is greater than X.

29 Claims, 29 Drawing Sheets

(52) U.S. Cl.
CPC ............ *A61B 19/5244* (2013.01); *A61B 19/26* (2013.01); *A61B 2019/502* (2013.01); *A61B 2019/505* (2013.01); *A61B 2019/5276* (2013.01)

(56) References Cited

U.S. PATENT DOCUMENTS

| | | | | |
|---|---|---|---|---|
| 5,623,582 | A * | 4/1997 | Rosenberg | 700/264 |
| 5,748,767 | A | 5/1998 | Raab | |
| 6,046,727 | A | 4/2000 | Rosenberg et al. | |
| 6,694,142 | B1 * | 2/2004 | Kuwahara et al. | 455/456.1 |
| 6,837,883 | B2 * | 1/2005 | Moll et al. | 606/1 |
| 2004/0039485 | A1 * | 2/2004 | Niemeyer et al. | 700/245 |
| 2005/0142525 | A1 * | 6/2005 | Cotin et al. | 434/262 |
| 2006/0012562 | A1 * | 1/2006 | Pope et al. | 345/156 |
| 2006/0116576 | A1 * | 6/2006 | McGee et al. | 600/434 |
| 2007/0013336 | A1 * | 1/2007 | Nowlin et al. | 318/568.21 |
| 2009/0030429 | A1 * | 1/2009 | Madhani et al. | 606/130 |

OTHER PUBLICATIONS

"PCT International Preliminary Report on Patentability", dated Jul. 29, 2008, for Application No. PCT/US2007/001897.
"PCT Written Opinion of the International Searching Authority", dated Jul. 29, 2008, for Application No. PCT/US2007/001897.
PCT Notification of Transmittal of the International Search Report and the Written Opinion of the International Searching Authority, or the Declaration, dated Jul. 26, 2007.
PCT International Search Report, dated Jul. 26, 2007.
PCT Written Opinion of the International Searching Authority, dated Jul. 26, 2007.

* cited by examiner

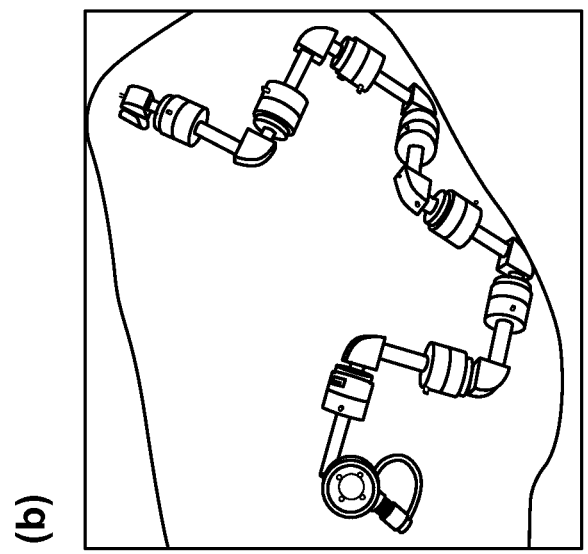
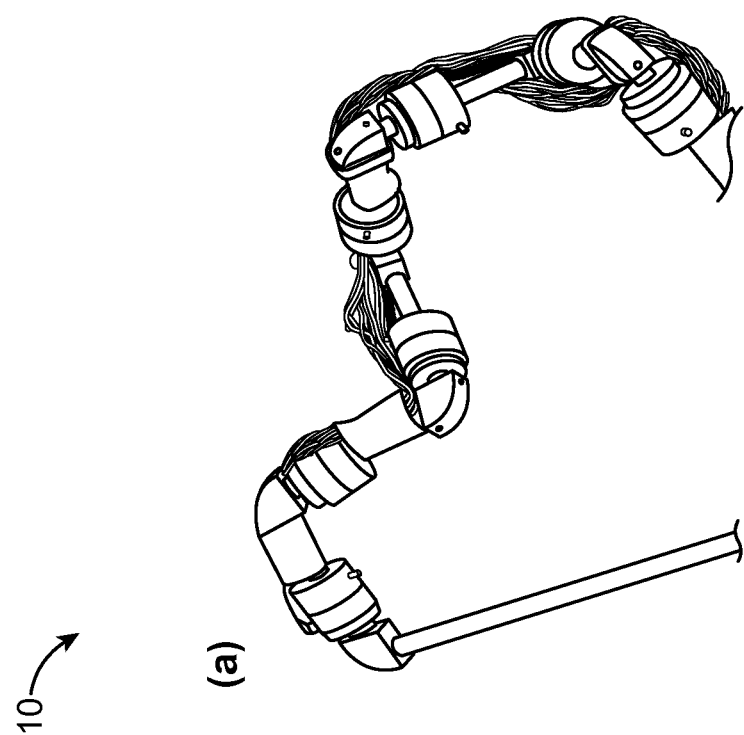
FIG. 5

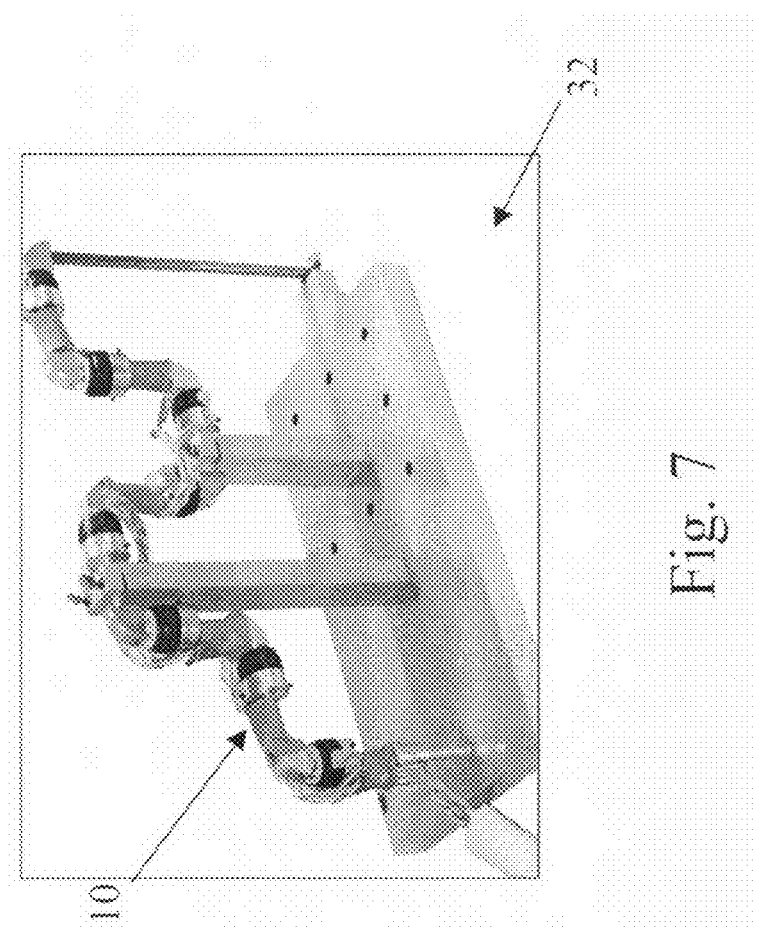

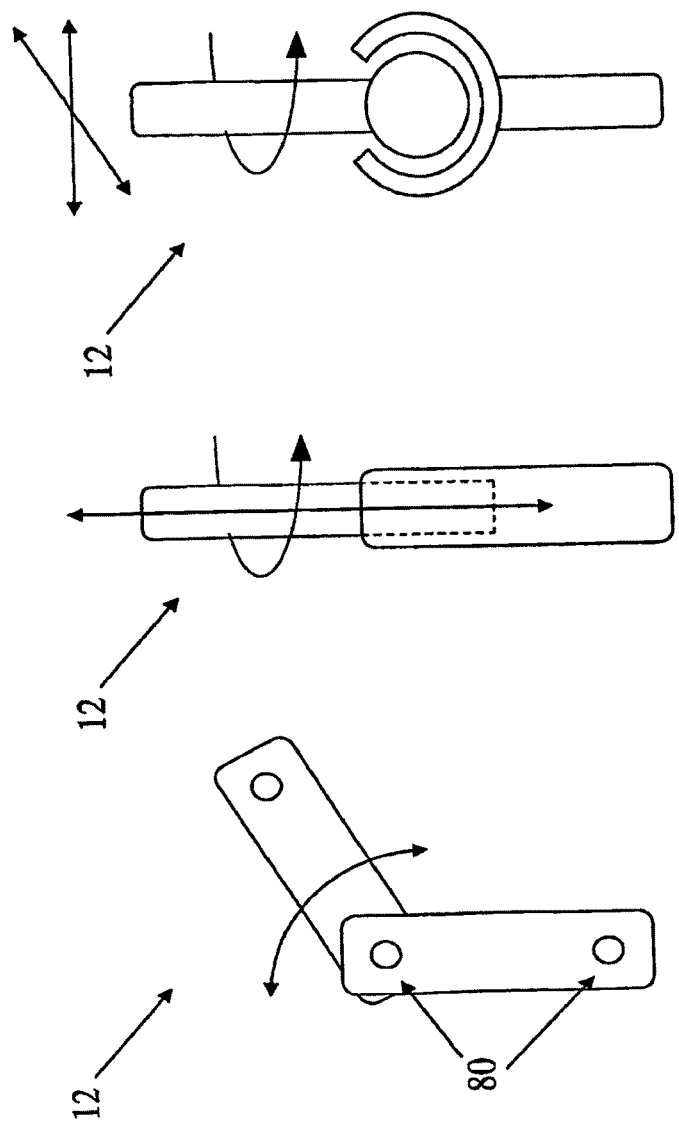

METHOD, APPARATUS, AND SYSTEM FOR COMPUTER-AIDED TRACKING, NAVIGATION AND MOTION TEACHING

CROSS-REFERENCE TO RELATED APPLICATIONS

This application claims priority from PCT patent application number PCT/US2007/001897, filed Jan. 24, 2007, which claims priority from U.S. Provisional Patent Application No. 60/761,702, filed Jan. 24, 2006, both of which are incorporated herein by reference.

STATEMENT REGARDING FEDERALLY-SPONSORED RESEARCH AND DEVELOPMENT

This invention was made, in part, with government support under a National Science Foundation Graduate Research Fellowship grant. The United States government may have certain rights in this invention.

FIELD OF THE INVENTION

The present invention is directed generally to methods, apparatuses, and systems for computer-aided tracking, navigation and motion teaching.

BACKGROUND OF THE INVENTION

Computer-aided tracking, navigation, and motion teaching are important tasks in a wide range of applications, including surgery and factory automation. The prior art contains technology directed to the tasks of computer-aided tracking, navigation, and motion teaching. However, the prior art is deficient in several areas, as will be discussed in more detail hereinbelow. Arthroscopy is a minimally invasive surgical procedure used to decrease the necessary incision size for joint repair surgery. Large operative incisions are replaced by small portal incisions. While a 15-25 cm opening is necessary to fully expose the hip joint using traditional methods (Scuderi G R and Tria A J. MIS of the Hip and the Knee: A Clinical Perspective. Springer-Verlag: New York. 2004.), arthroscopy only requires two or three portals of approximately 6-7 mm (Safran M R, Stone D A, Zachazewski J. Instructions for Sports Medicine Patients. Elsevier Inc.: Philadelphia. 2003.). A long thin camera, called an arthroscope, is placed in one portal to display 44 the joint area that would otherwise require a full-size incision to expose. Additional portals are employed for the insertion of surgical tools. FIG. 1 illustrates a prior art arrangement for hip arthroscopy. As shown in FIG. 1, the surgeon navigates a surgical tool by using only camera images displayed on an operating room screen.

Arthroscopy was initially introduced as a diagnostic tool, but now has significant advantages for many joint repair procedures (See, for example, Villar R N. Hip Arthroscopy. Butterworth-Heinemann Ltd.: Oxford. 1992.). Advantages such as a faster recovery time, shorter hospital stay, less soft tissue trauma, less blood loss, and a lower incidence of infection make arthroscopic surgery more desirable than traditional full-incision operations (See, for example, Scuderi G R and Tria A J. MIS of the Hip and the Knee: A Clinical Perspective. Springer-Verlag: New York. 2004.). Hip arthroscopy can be used for removing loose bodies, smoothing rough bone surfaces, and trimming damaged or abnormal bone and tissue (See, for example, Safran M R, Stone D A, Zachazewski J. Instructions for Sports Medicine Patients. Elsevier Inc.: Philadelphia. 2003.). Also, minimally invasive treatment of early hip problems could decrease or delay the onset of other more serious hip conditions (See, for example, McCarthy J C, Noble P C, Schuck M R, Wright J, Lee J. The Role of Labral Lesions to Development of Early Degenerative Hip Disease. Clinical Orthopaedics and Related Research, 2001; 393:25-37; and Ganz R, Parvizi J, Beck M, Leunig M, Notzli H, Siebenrock K A. Femoroacetabular Impingement. Clinical Orthopaedics and Related Research. 2003; 417:112-120.).

Despite the benefits of arthroscopic surgery, arthroscopy is not as common in hip repair as in knee and shoulder repair. The hip joint introduces additional challenges for arthroscopy. For example, the hip joint is located deeper within the body than joints such as the knee or shoulder. Also, the ball and socket geometry of the joint provides a very tight working envelope. Finally, there are an increased number of surrounding muscles, ligaments, and neurovascular structures to consider in the case of the hip joint.

The challenges associated with the hip have created two particular obstacles for arthroscopic hip surgery: awareness of spatial orientation during joint navigation; and portal incision placement while avoiding damage to critical anatomical structures. Although the arthroscope allows the surgeon to observe the joint, extra skill is required to associate the camera image with the actual patient anatomy for navigation. This is a common problem for other minimally invasive surgeries including MIS hip replacement and laparoscopic procedures (See, for example, Scuderi G R and Tria A J. MIS of the Hip and the Knee: A Clinical Perspective. Springer-Verlag: New York. 2004.; and Schijven M, Jakimowicz J. Face-, expert, and referent validity of the Xitact LS500 Laparoscopy Simulator. Surgical Endoscopy. 2002; 16:1764-70.). Instrument placement is a critical step in establishing the desired arthroscope viewing area. Multiple arteries, veins, and nerves populate the area in which the portal incisions are placed. The surgeon's challenge is to create incisions that provide appropriate access to the joint, but do not harm the sciatic nerve, femoral artery, or femoral vein. The surgeons who perform this procedure rely heavily on intuition gained through experience to overcome these challenges.

Computer-aided tools are appearing more frequently to assist in medical procedures and as training simulators. For example, hip replacement systems enable the surgeon to place implants more accurately and consistently (See, for example, DiGioia A M, Simon D A, Jaramaz B, Blackwell M, Morgan F, O'Toole R V, Colgan B, Kischell E. HipNav: Pre-operative Planning and Intra-operative Navigational Guidance for Acetabular Implant Placement in Total Hip Replacement Surgery. In: Computer Assisted Orthopaedic Surgery Symposium; 1995 Nov. 30-Dec. 2; Bern, Switzerland; and Taylor R H, Mittelstadt B D, Paul H A, Hanson W, Kazanzides P, Zuhars J F, Williamson B, Musits B L, Glassman E, Bargar W L. An Image-Directed Robotic System for Precise Orthopaedic Surgery. IEEE Transactions on Robotics and Automation. 1994; 10(3):261-275.). A system for minimally invasive coronary bypass surgery assists with incision accuracy and visualization of the tool within the patient (See, for example, Chiu A M, Boyd D, Peters T M. 3-D Visualization for Minimally Invasive Robotic Coronary Artery Bypass (MIRCAB). In: 22nd Annual EMBS International Conference; 2000; Chicago Ill.). Training simulators are currently under research for procedures such as laparoscopic and minimally invasive heart surgery (See, for example, Schijven M, Jakimowicz J. Face-, expert, and referent validity of the Xitact LS500 Laparoscopy Simulator. Surgical Endoscopy. 2002; 16:1764-70; and Rotnes J S, Kaasa J, Westgaard G, Eriksen E M, Hvidsten P O, Strom K, Sorhus V, Halbwachs Y, Jakob O, Fosse E. Realism in surgical simulators with freeform geometric modeling. In: Lemke H U, Vannier M W, Inamura K, Farman A G, Doi K, editors. Computer Assisted Radiology and Surgery; 2001; Berlin, Germany. Elsevier; 2001. p. 997-1002.). While these and other tools have been introduced to supplement a surgeon's abilities, a similar tool for arthroscopic hip surgery does not exist. One embodiment of the present invention focuses on the particular issues of portal placement and instrument navigation in arthroscopic hip surgery.

Position tracking is also an important component of many other computer-aided surgical systems. Optical and electromagnetic systems are the most common types of tracking devices, but these systems have limitations. For instance, an optical system can lose information from its position sensors if the line of sight to the receiver is broken. Optical systems such as those provided by Northern Digital Inc. or Advanced Realtime Tracking (ART) are more accurate than electromagnetic systems for medical applications, but are relatively expensive (See, for example, Birkfellner W, Watzinger F, Wanschitz F, Ewers R, Bergmann H. Calibration of tracking Systems in a Surgical Environment. IEEE Transactions on Medical Imaging. 1998; 17(5):737-42; Advanced Realtime Tracking (homepage on the Internet). Mar. 25, 2005. Available from: http://www.ar-tracking.de/; Northern Digital Inc. (homepage on the Internet). Mar. 25, 2005. Available from: http://www.ndigital.com/certus.php). While less expensive, electromagnetic systems are susceptible to distortion or noise from other metallic objects or stray magnetic fields. More complex or hybrid systems which combine both technologies are currently under research (See, for example, Schwald B, Seibert H. Registration for a Hybrid Tracking System 40 for Medical Augmented Reality. Journal of WSCG. 2004; 12(1-3).).

Mechanical tracking systems avoid the occlusion and distortion issues, but few mechanical systems exist. The few available products, such as the Faro Arm (See, for example, Faro Technologies (homepage on the Internet). Feb. 18, 2006. Available from: http://www.faro.com/), are too large and heavy to be easily manipulated. Due to their associated problems, the existing tracking devices listed above have significant drawbacks.

Position tracking is also important in fields other than the medical field. For example, position tracking is important in many industrial applications. In particular, the manufacturing and assembly industries are using increasing numbers of robots and other computer controlled machines. These machines are often used in the space previously occupied by human workers. As a result, the robots must not only be "trained" to do the proper job, but they must be trained to do the proper job within certain constraints. For example, robots must often operate within a particular space, so as not to interfere with other robots, with human workers, or with other obstacles. The prior art process of teaching a robot is tedious and time consuming. As a result, the efficiencies of robots are slow to be realized or are not being realized to their full potential.

In other applications, position tracking is important for recreating objects, such as one of a kind objects handmade by skilled artisans. Thereafter, it may be necessary to translate the handmade objects into information that can be used by computer controlled manufacturing processes to manufacture the objects in large numbers, to create computer-generated images and models of the objects, or to otherwise analyze or work with the objects. Several processes exist for such tasks, although they typically require relatively large and bulky machines that do not work well with objects having hard to reach surfaces.

Accordingly, there is a need for improved apparatuses and methods for use with computer aided tools, particularly for position tracking although not limited thereto. Those and other advantages of the present invention will be described in more detail hereinbelow.

BRIEF SUMMARY OF THE INVENTION

The present invention is directed generally to methods, apparatuses, and systems for computer-aided navigation, tracking, and motion teaching. There are many applications and embodiments of the present invention. In some embodiments, the present invention may be used to ease the difficulty associated with arthroscopic hip surgery. While arthroscopic surgery has many advantages over traditional surgery, this minimally invasive technique is not often applied to the hip joint. Two main reasons for this are the complexity of navigating within the joint and the difficulty of correctly placing portal incisions without damaging critical neurovascular structures. The present invention discloses a computer-aided navigation system to address the challenges of arthroscopic hip surgery. Unlike conventional arthroscopic methods, the present invention uses a hyper-redundant tracking device to track surgical instruments, thus eliminating the occlusion and distortion problems associated with standard optical and electromagnetic tracking systems. In such embodiments, a tracking device of encoders may be employed to track the motion of surgical tools during an operation, and produce computer generated images of real-time motion of the tools relative to the patient anatomy. In this way the present invention can be used to supplement the restricted view from a typical arthroscopic camera. Ultimately, the proposed computer-aided navigation system can increase the use of advantageous arthroscopic procedures over full-incision operations in the hip joint.

In other embodiments, the present invention may be used for biopsies and to create images of targeted areas. For example, the present invention may be used with an ultrasound device to scan an area and to create two-dimensional and three-dimensional images. Thereafter, for example, the present invention may be used with a medical device, such as a biopsy needle, to create a computer generated image of the medical device (e.g., biopsy needle) in the two-dimensional or three-dimensional image created with the ultrasound device. In this way, the present invention allows the user to view a computer generated image of the medical device being used in an area (such as within the body) that is not visible. For example, the present invention may be used to navigate a biopsy needle to a target tissue region more quickly and accurately.

In other embodiments, the present invention may be used with industrial robots. For example, the present invention may be used in teaching industrial robots, such as in establishing a robot's working envelope and defining and programming movements for robots. The present invention may also be used with industrial robots for teaching the motion of the robot for particular tasks. In other embodiments, the present invention may be used for measuring the shape and position of a workspace. For example, the present invention may be used for tracing a target line for arc welding. Those and other uses and embodiments are possible with the present invention.

The present invention addresses problems in the prior art and is an effective alternative to more expensive and often problematic prior art tracking systems. For example, some prior art device rely on optical communications and, therefore require a clear line of sight for proper operation. In other prior art solutions, the devices are affected by metal objects which can interfere with electromagnetic communications systems used by the prior art. In other prior art devices, the range of motion is limited and, therefore, the device cannot reach all target locations. This is particularly problematic in prior art devices operating in an enclosed space or in the presence of barriers and obstacles. The present invention, however, overcomes these drawbacks with the prior art, as will be discussed in more detail hereinbelow. For example, some embodiments of the present invention use a combination of articulated links having six or more degrees of freedom that provide improved flexibility for maneuvers while tracking instrument position.

The present invention includes methods for performing the tasks described herein, systems constructed according to the present invention, and devices constructed according to the present invention. The present invention can also include or be embodied as computer software which, when executed by a processor, causes the processor to perform certain actions according to the present invention. Although the present invention will often be described in the context of hip surgery, biopsies, and industrial robots, the present invention is not limited to such applications. For example, the present invention is applicable to other surgical procedures and to industrial and commercial applications other than teaching robots. Many additional features are also possible with the surgical embodiments of the present invention. For example, some embodiments may include a visual, audible, or other warning to inform the user, such as a doctor, of dangerous or forbidden maneuvers. These and other teachings, variations, and advantages of the present invention will become apparent from the following detailed description of the invention.

BRIEF DESCRIPTION OF THE SEVERAL VIEWS OF THE DRAWING

Embodiments of the present invention will now be described, by way of example only, with reference to the accompanying drawings for the purpose of illustrating the embodiments, and not for purposes of limiting the invention, wherein:

FIGS. 5a and 5b illustrate a tracking device for position tracking according to one embodiment of the present invention. The tracking device is redundant with extra degrees of freedom, to increase flexibility and ensure the tracking device remains out of the surgeon's work space. FIG. 5a illustrates one embodiment of a tracking device according to the present invention, and FIG. 5b illustrates one embodiment of a tracking device applied to a hip.

FIG. 6a illustrates one embodiment of tracking device components, and FIG. 6b is a diagram of one embodiment of an assembled link.

FIG. 7 illustrates one embodiment of a tracking device locked in initialization configuration for the calibration of encoders.

FIG. 10a illustrates a window showing the simulated arthroscope view, and FIGS. 10b-d illustrates computer generated views of hip from alternate perspectives. The windows illustrated in FIGS. 10b-d can be modified by the user to show a desired viewpoint.

FIG. 11a illustrates an arthroscopes with 0° (top), 30° (center), and 70° (bottom) viewing angles. FIG. 11b illustrates a computer generated view from an arthroscope with 0° viewing angle. FIG. 11c illustrates a computer generated view from an arthroscope with 70° viewing angle.

FIG. 12a illustrates a sphere representing a safe area for tool operation. FIG. 12b illustrates an arthroscopic view from within the safe sphere. FIG. 12c illustrates an arthroscopic view from outside of the safe sphere.

FIG. 13a illustrates the model of a human hip joint. FIG. 13b illustrates an arthroscope and tracking device applied to the model.

FIG. 14a illustrates a computer generated 70° arthroscope view, and FIG. 14b illustrates an actual 70° arthroscope view.

FIGS. 27-29 illustrate additional embodiments of links according to the present invention.

DETAILED DESCRIPTION OF THE INVENTION

The present invention is directed generally to methods, apparatuses, and systems for computer-aided tracking, navigation, and motion teaching. The present invention has many applications, such as in medical care and in industrial manufacturing, as well as in other fields. The present invention has many specific applications, such as tracking medical tools in the body during medical procedures, generating images of medical tools in the body during medical procedures, in robot teaching, in process simulation, in path planning, and in other applications.

Figure 1:
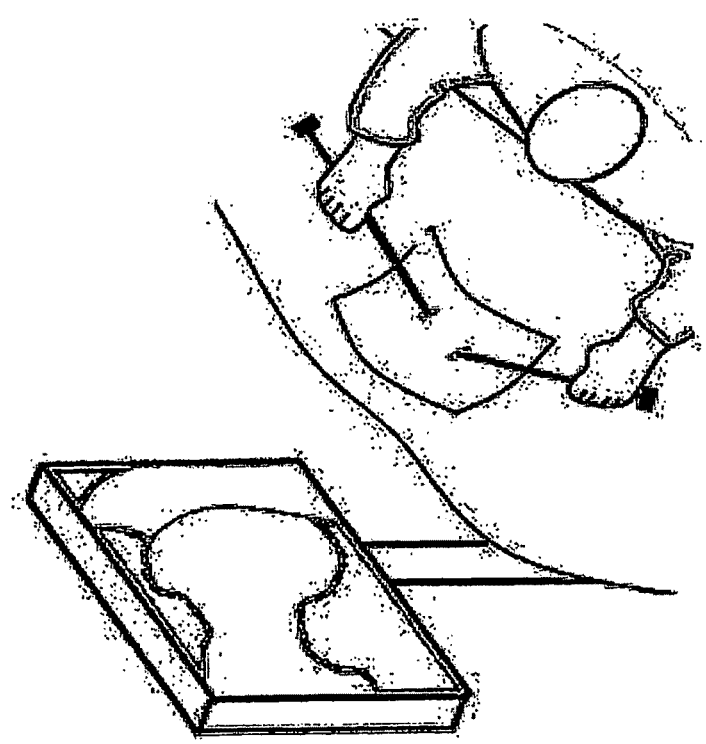
FIG. 1 illustrates a standard arrangement for prior art hip arthroscopy. An arthroscope and other surgical tools are manipulated by the surgeon through small portal incisions in the patient. The surgeon navigates using the arthroscope image displayed on a computer screen in the operating room.
Figure 2:
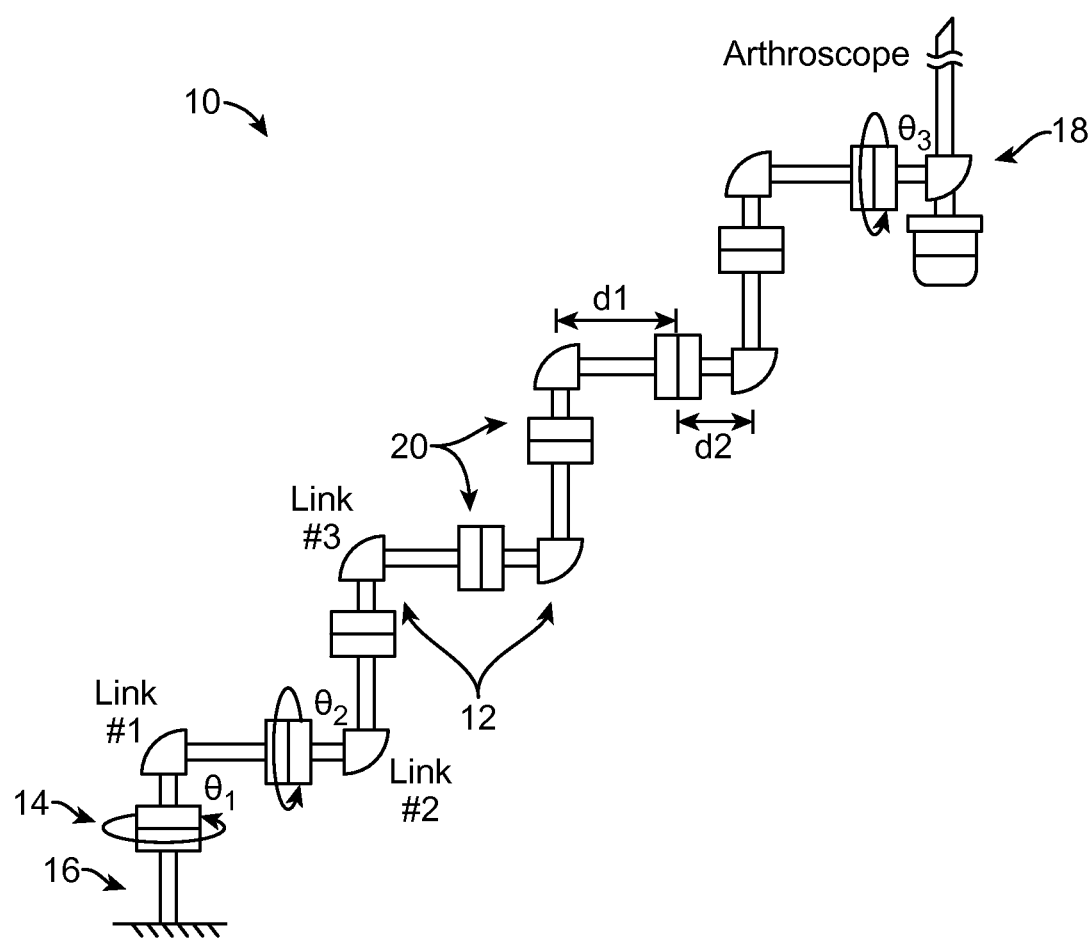
FIGS. 2, 3, 4a and 4b illustrate several embodiments of the tracking device according to the present invention.

FIG. 2 illustrates one embodiment of a tracking device 10 according to the present invention. The tracking device 10 includes a plurality of links 12 connected together. The tracking device 10 in the illustrated embodiment includes a reference end 14 connected to a reference pin or some other reference point 16, and a working end 18 for moving and/or for engaging other objects. In some embodiments, the working end 18 may be a tool or other device attached to the end of the tracking device 10. For example, the tool may be rigidly attached to the link 12 closest to the working end 18 of the device 10. The tracking device 10 may include other components not shown in FIG. 2, such as sensors 22, communications paths, power paths, power sources, actuators, processors, memory, and other components.

The present invention will generally be described in terms of a tracking device 10 having eight degrees of freedom, although the tracking device 10 may have more or less than eight degrees of freedom. Furthermore, the tracking device 10 will generally be described in terms of adjacent links 12 having one degree of freedom. However, as will be described in more detail hereinbelow, the present invention may include combinations of links 12 having more than one degree of freedom.

The present invention will also be described, generally, in terms of a device 10 in which a spatial position is determined by measuring the relative positions of several links 12 in more degrees of freedom than is required to determine the spatial position. For example, as stated above, the present invention will often be described in the context of a device 10 having eight degrees of freedom, although fewer than eight degrees of freedom are required to determine a spatial position in a three dimensional space. In other embodiments, such as embodiments in which a position is determined in a two dimensional space, fewer degrees of freedom are required. In other embodiments, additional degrees of freedom are required, such as when it is necessary to determine a both position in space and an orientation of a tool or other object at that position in space.

Many variations are possible with the present invention, some requiring more degrees of freedom and some requiring fewer. However, the present invention will be described in the context of a device 10 in which additional degrees of freedom are measured and used for determining spatial and/or other orientations. For example, if "X" degrees of freedom are the minimum number of degrees of freedom that must be measured to make a determination of position and/or orientation, then the present invention will use a tracking device 10 having and measuring "Y" degrees of freedom, where Y is greater than X. The number of additional degrees of freedom (i.e., the difference between Y and X) can vary depending on the specific results desired. The advantages of measuring additional degrees of freedom according to the present invention will be described in more detail hereinbelow.

The links 12 will generally be described in terms of "L"-shaped links. However, the links 12 may have other shapes. For example, the links 12 may be "C"-shaped or the links 12 may be straight with a joint 20 between the links 12 that provides for desired movement between links 12. Furthermore, the links 12 may all be the same or they may be different in size or shape. For example, some tracking devices 10 may include both "L"-shaped links and "C"-shaped links. In other embodiments, the size of the links 12 may vary. As used herein, "link" 12 generally refers to a rigid body, and the degrees of freedom come from joints 20 between the links 12. The joints 20 may be any moveable connection between the links 12. Joints 20 may, for example, pivot, rotate, telescope, or otherwise provide for movement between links 12.

The joints 20 may be low friction devices to allow the device 10 to move freely and easily. Alternatively, the joints 20 may have significant friction or resistance to motion. This friction may be a consequence of the particular design or manufacture of the joint 20, such as when cost is more important than allowing the device to move freely. Alternatively, resistance to motion may be intentionally designed into the joint 20. For example, the joints 20 may include friction fittings to introduce resistance to motion of the joints 20. In other embodiments, electromagnets may be included in the joints 20 to selectively hold links 12 together when energized and provide little or no resistance to movement when de-energized. Similarly, electromechanical devices may be used to engage or disengage moving parts and, thereby, introduce resistance to motion. Such selective resistance may be controlled, for example, with a button or knob on the device, through a computer interface such as mouse, keyboard, or touchscreen, or otherwise.

The amount of resistance to motion intentionally introduced into the joints 20 can vary depending on the particular application. In some embodiments, the resistance to motion may be sufficient to allow the device 10 to maintain a shape or configuration under its own weight, but not so much as to prevent a user from changing the shape or configuration. The resistance to motion may be constant or it may be variable. More or less resistance may be introduced depending on the particular application. The use of friction in the joints 20 is advantageous, for example, if at least part of the device 10 must be positioned or configured above the ground. In such applications, the use of resistance in joints 20 allows the device 10 to maintain a configuration under its own weight, thereby allowing a user to work without manually supporting the device 10 in the air and without using mechanical supports for the device 10. For example, in some applications of robot teaching the workspace is limited and the particular configuration of the robot must conform to certain space restrictions. For example, the robot must not interfere with adjacent machinery, people, or other robots. In those applications, it is advantageous for the device 10 to hold its general shape while the user modifies certain aspects of the device's configuration. This feature also has advantages in other applications.

Sensors 22 are illustrated, for example, hereinbelow in FIG. 6. The sensors 22 are located in each link 12 and may be encoders or other devices for tracking the movement and position of a link 12 relative to an adjacent link 12 are located in each link 12. The encoders 22 may be absolute encoders or incremental encoders. Tracking devices 10 using incremental encoders 22 may also be used with initialization devices 32, as will be described in more detail hereinbelow. Devices utilizing more than one degree of freedom between links 12 may include an encoder for each degree of freedom to accurately determine the movement and position of the link 12 relative to an adjacent link 12, or they may use other devices to track more than one degree of freedom. Although the present invention will generally be described in terms of "encoders", other types of sensors 22 may be used to determine the movement or position of the links 12 and the present invention is not limited to the used of encoders.

Communications paths 24 are illustrated, for example, hereinbelow in FIG. 6. Communications paths 24 may be inside or outside of the tracking device 10. The communications paths 24 may be, for example, electrical wires, optical fiber, or other communications paths. In some embodiments, the tracking device 10 may utilize wireless communications to transmit information to a receiver. For example, the tracking device 10 may include transmitters and/or receivers in each link 12 to transmit information about the position of the link 12 to another location. In other embodiments, low power, short range transmitters may be used and links 12 may relay information along the tracking device 10 from one link 12 to another link 12 and finally to a storage or processing device, such as the computer described hereinbelow.

Power paths 26 are illustrated, for example, hereinbelow in FIG. 6. Power paths 26 may be inside or outside of the tracking device 10. For example, electrical wires may be used to carry power to various parts of the tracking device 10. In other embodiments, local power sources, such as batteries, may be used in some or all of the links 12 in the tracking device 10.

The tracking device 10 according to the present invention will generally be described as a redundant tracking device 10, meaning that it has more than six degrees of freedom. Having additional degrees of freedom offers many advantages. For example, having additional degrees of freedom allows the tracking device 10 to move more smoothly, reduces binding of the tracking device 10, and allows the tracking device 10 to assume many positions between any two points. The last point is particularly important because it allows the tracking device 10 to maintain a particular reference point and end point and still allow for the middle of the tracking device 10 to be moved. This is particularly helpful when the tracking device 10 is used in medical procedures.

As discussed above, tracking devices 10 having more than six degrees of freedom offer significant advantages. However, some advantages of the present invention may still be realized with tracking devices 10 having only six degrees of freedom. Furthermore, some advantages of the present invention may be realized with tracking devices 10 having less than six degrees of freedom. For example, a tracking device 10 that does not need the freedom to move in all three dimensions may have less than six degrees of freedom and still realize some of the advantages of the present invention.

Figure 3:
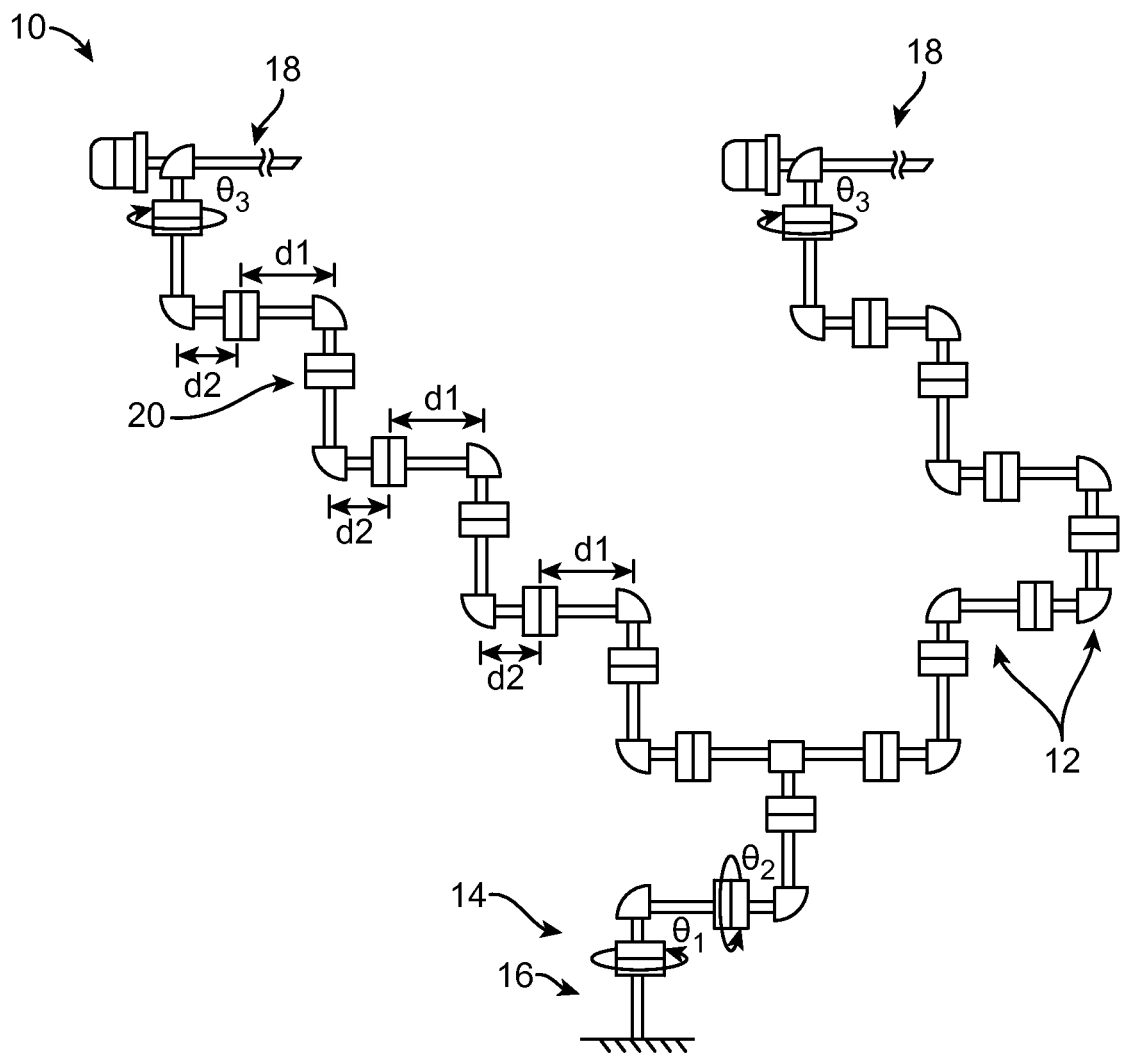

FIG. 3 illustrates another embodiment of a tracking device 10 in which the tracking device 10 has more than two working ends 18. This embodiment of the invention provides for advantages in certain applications such as, for example, when multiple working ends 18 are required but limited space is available near the reference end 14. Many other variations of the tracking device 10 are possible. For example, the tracking device 10 may include more than two working ends 18, more than two reference ends 14, and other variations.

Figure 4A:
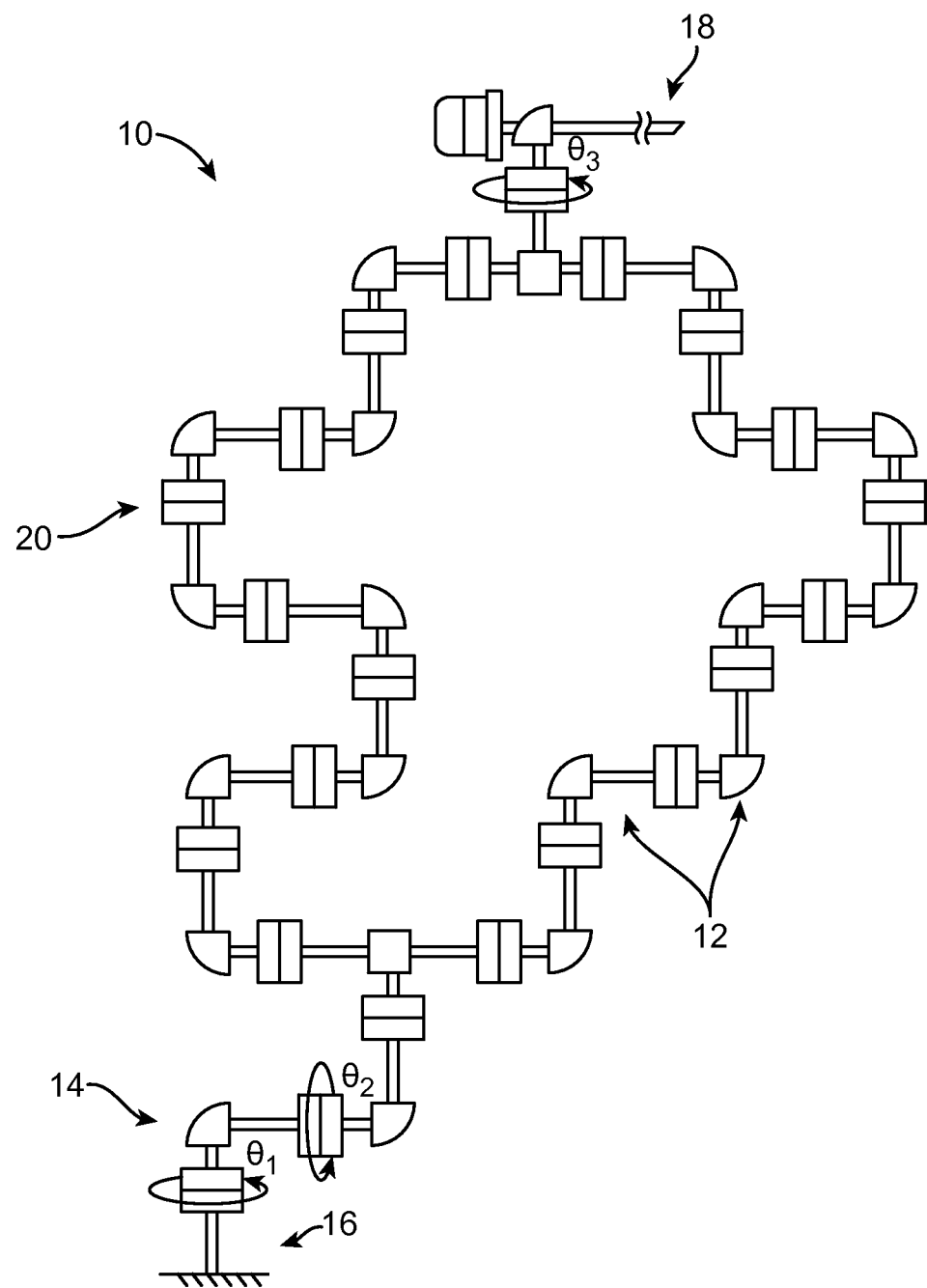

FIG. 4a illustrates an embodiment of a tracking device 10 in which there are two sets of links or paths between the working end 18 and the reference end 14. These sets of links or paths between the working end 18 and reference end 14 will sometimes be referred to as "middle portions". This embodiment of the present invention may offer advantages in accurately determining the position of the working end 18 because the redundant middle portions of the tracking device 10 provide independent measures of a significant portion of the device 10. Accuracy of the present invention is discussed in more detail hereinbelow.

Figure 4B:
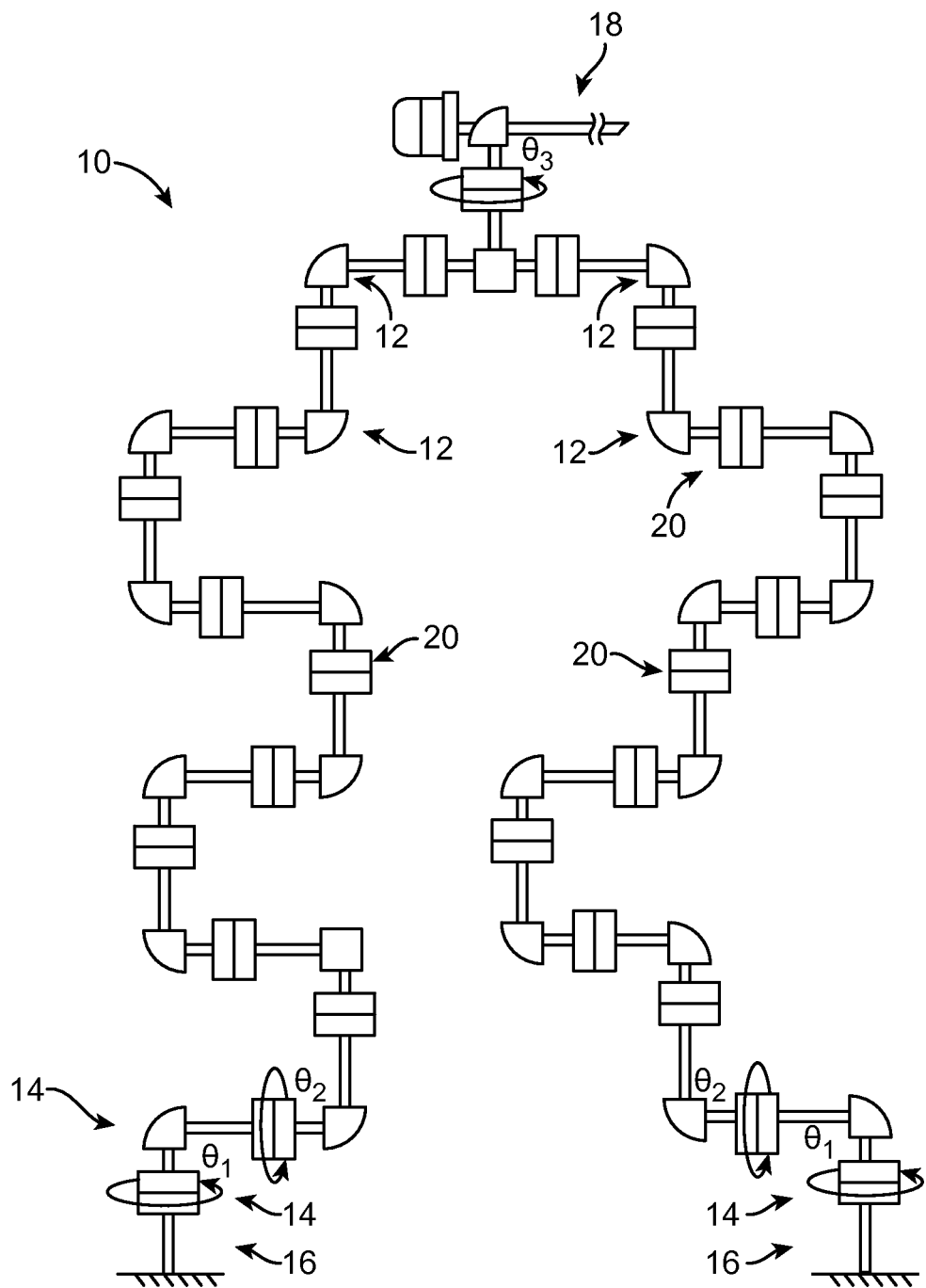

FIG. 4b illustrates another embodiment of the tracking device 10 in which there are two sets of links 12 connecting the working end 18 to two reference ends 14. More than two sets of links 12 and more than two reference ends 14 are also possible in tracking devices 10 according to the present invention.

FIG. 5a illustrates another embodiment of the tracking device 10. In the illustrated embodiment, the tracking device 10 is redundant with extra degrees of freedom to increase flexibility and ensure the device 10 remains out of the surgeon's work space. In FIG. 5b, the tracking device 10 lies against the patient and does not protrude into the working area.

Figure 6A:
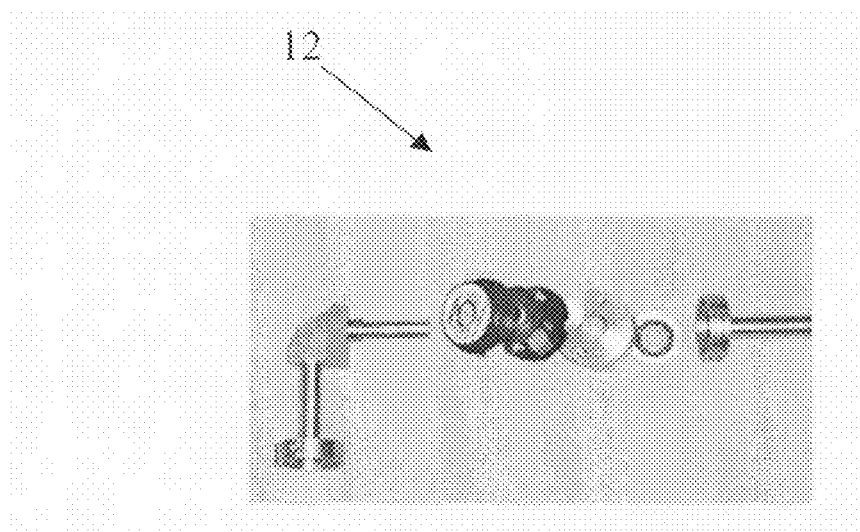
FIGS. 6a and 6b illustrate one embodiment of encoder link components and assembly.
Figure 6B:
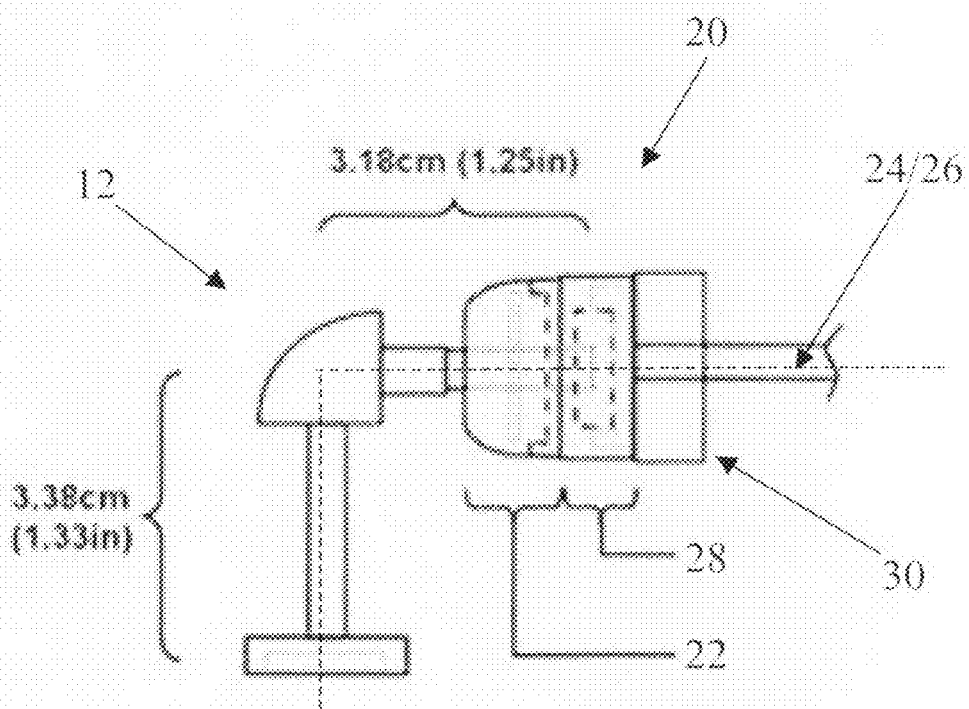

FIGS. 6a and 6b illustrate one embodiment of link 12 components and assembly. The main components of the tracking device 10, as diagramed in FIG. 6, are the "L" shaped links 12, the encoders 22 which may be obtained, for example, from US Digital Corporation, communications paths 24, power paths 26, and the rotational bearings 28. The encoders 22 may be, for example, US Digital E4 encoders. The 90° bend in the links 12 place the next joint 20 axis of rotation perpendicular to the previous joint 20 axis.

In the illustrated embodiment, the encoder 22 diameter is 2.16 cm (0.85 in) with a resolution of 300 counts per revolution. Using the encoder's 22 two-channel quadrature output, 1,200 pulses per revolution are achieved. The encoders 22 have three parts: the base with the light source and receiver, the encoder disk with alternating reflective and non-reflective bands to quantify rotation, and a protective outer cover. The base of the encoder 22 is fixed to a plate connected to one link 12 while the encoder disk is attached to the next link 12 in the sequence. Thus, the encoder 22 measures the rotation between links 12 as the disk rotates relative to the encoder base. Adjacent links 12 are attached via a bearing connection 28.

In some embodiments, adjacent links 12 are attached via a bearing 20 connection with full 360-degree motion. Providing 360 degrees of motion makes the device 10 easier to use, but it also adds complexity to the device 10. In some embodiments, the adjacent links 12 have less than 360 degrees of rotation, thereby simplifying the device 10. Although the external power and communications cables 24, 26 can hinder excessive rotation, in many applications this is not a concern because each link 12 typically rotates within a small range of angles due to the extra degrees of freedom in the tracking device 10.

The links 12 and joint 20 may also include additional parts and components. For example, the joint may include an actuator 30, such as an electric motor or solenoid, to cause relative motion between adjacent links 12. The actuator 30 may be connected between links 12, connected between a link 12 and the encoder 22, or otherwise connected so as to cause movement of one link 12 relative to an adjacent link 12. The actuator 30 is illustrated as being adjacent to the bearings 28 and away from the encoder 22, although other orientations of the actuator 30, bearings 28, and encoder 22 are possible, as well as integration of one or more of those components together or into another part of the apparatus.

The position and orientation of the surgical instruments or other objects used with the present invention can be determined through two main homogeneous transformations. The coordinate frame attached to the endpoint of the tracking device 10 must be determined in model coordinates. In the context of a medical device, the first transform, $T_1$, calculates the tool position relative to the pelvic pin. The eight encoder angles are used to determine this transformation, and $T_1$ is recalculated to update the tool position each time the encoder angles change. A data acquisition device, such as the USB1 from US Digital Corporation, was used to obtain the encoder angles. A second transform, $T_2$, moves from the pin frame to the model frame. This transform will be calculated only once, based on the pin position in the 3-D patient model obtained from x-rays (See, for example, Gunay, M. Three-dimensional bone geometry reconstruction from x-ray images using hierarchical free-form deformation and non-linear optimization [dissertation].Pittsburgh (Pa.): Carnegie Mellon University; 2003.).

FIG. 7 illustrates one embodiment of a tracking device 10 locked in an initialization configuration. Embodiments of the present invention that use incremental encoders 22 must be initialized to mark a zero degree rotation at a known location. In the illustrated embodiment, the tracking device 10 is placed on the initialization device 32 shown in FIG. 7, which is a precisely machined plate with an attachment pin and tracking device 10-positioning posts. The tracking device 10 is fixed into the initialization device 32 to accurately position of the tracking device 10 in a predetermined orientation before its use. Based on the known configuration for the initialization, the encoder angles are used to determine the transformation matrices for the end point of the tracking device 10 relative to the hip reference pin. Different initialization devices 32 may be used with the present invention. Alternatively, the present invention may be used without an initialization device 32, such as by using absolute encoders 22 or other reference or initialization methods.

Figure 8:
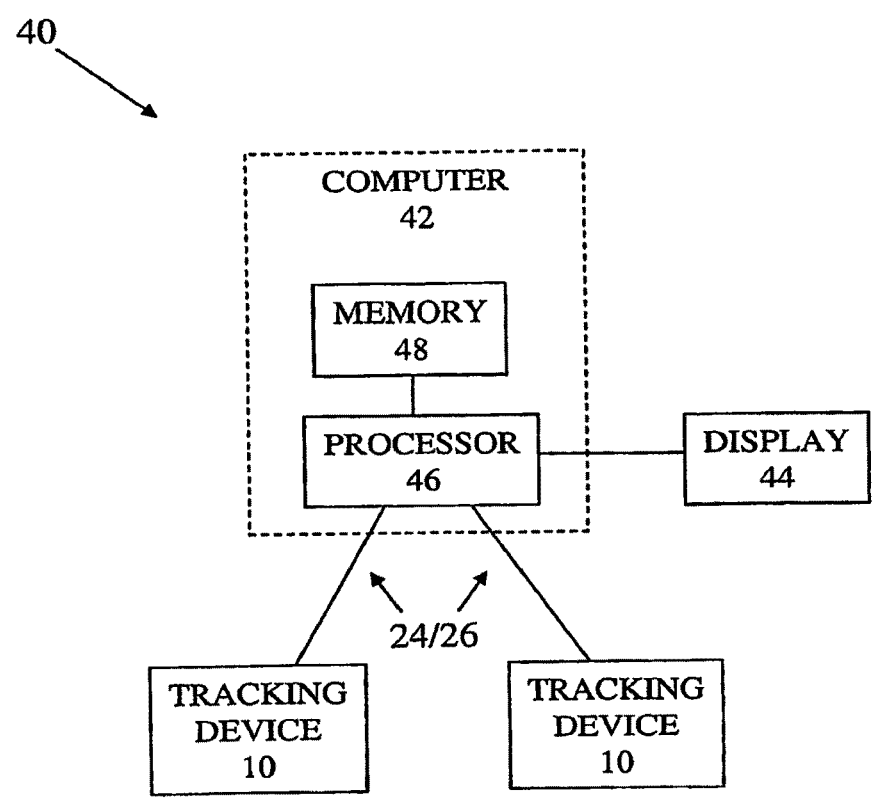
FIG. 8 illustrates one embodiment of a tracking device and computer used according to the present invention.

FIG. 8 illustrates one embodiment of a system 40 according to the present invention including two tracking devices 10, a computer 42, and a display 44. Data from the tracking devices 10 is sent to the computer 42, which processes the data and sends data to the display 44 to produce images. The computer 42 includes a processor 46 and memory 48. The memory 48 may include, for example, data from the tracking devices 10, data regarding the specific applications for which the system 40 is used, or other information. For example, the memory 48 may include images for a medical procedure, rules for a manufacturing process, or other information. The memory 48 may also include computer software or other computer-readable instructions which, when executed by the processor 46, causes the processor 46 to perform one or steps according to the present invention. For example, the computer software may process the data from the tracking device 10 and produce computer-generated images on the display 44.

Many variations of the system 40 are possible. For example, the system 40 may include more or less than two tracking devices 10. The system 40 may include more than one display 44 and more than one computer 42. The system 40 may include a computer 42 having more than one processor 46, more than one memory 48, and additional components. The system 40 may also include other variations. For example, the computer 42 may output signals to a device other than or in addition to a display 44. In some embodiments, the system 40 may not include the display 44. In some embodiments, the computer 42 may output signals to a robot that is being trained or otherwise used with the present invention. The computer 42 may also include additional inputs, such as an input from an ultrasound device or input from a robot or other device being used with the present invention.

In some embodiments, one or more tracking devices 10 may be made relatively small and embedded in objects such as clothing. Thereafter, the movements of the person wearing the clothing may be tracked and measured. This information may be used, for example, in creating computer generated humanoid motions, such as in video games, animated movies, and other applications. The information also has other applications, such as monitoring the state of people who are at risk of falling. In some applications, the system 40 may be program to recognized certain warning signs, such as a person falling down, clutching their chest, or other actions. If the system 40 detects a potential danger condition it may be programmed to send a warning, such as via a wireless transmitter, to call for assistance. In some applications, the computer 42 may be attached to the person wearing the device. In other applications, where the user will not be traveling far, the computer 42 may be located away from the person and the information captured via wireless transmissions or via electrical, optical, or other wired connection.

Figure 9:
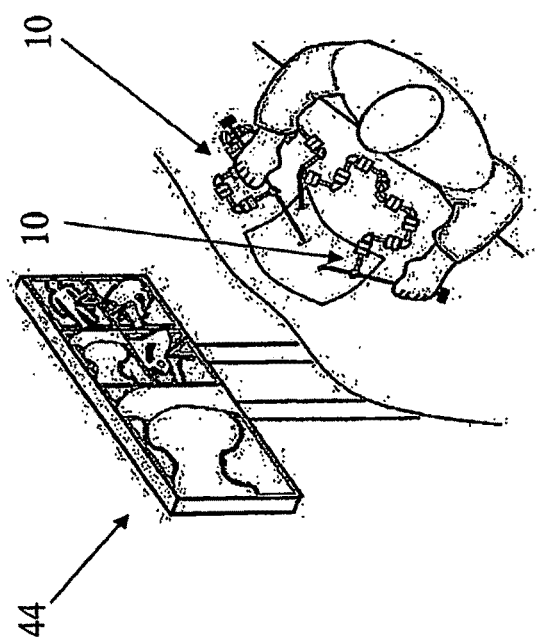
FIG. 9 illustrates a computer-aided navigation system for arthroscopic hip surgery using a tracking device tracking mechanism according to the present invention. Two tracking devices track the position of the surgeon's arthroscope and other tools. An additional screen in the operating room displays computer images of instruments and the patient anatomy from multiple views.

FIG. 9 illustrates another embodiment of the present invention. That embodiment is illustrated in the context of a medical device, although variations of the illustrated embodiment have other applications as will be described below.

In many surgical applications, the tool motion is limited around the portal incisions. As a result, the use of a tracking device 10 according to the present invention offers many advantages and is well suited to arthroscopic surgery. The portals themselves prevent significant instrument motion, thus a flexible tracking device 10 will not unduly interfere with the arthroscopic procedure. Also the tracking device 10 length can be optimally designed since the portals are only made in specific anatomic locations.

FIG. 9 shows a navigation system 40 with two tracking devices 10 and a display 44. The tracking devices 10 capture the tool or device position, orientation, and motion relative to the patient's anatomy. The working end 18 of the tracking device 10 is a medical tool or device, such as a scalpel or an arthroscope. The reference end 14 of the tracking device 10 is attached to a reference pin (not shown in FIG. 9). The reference pin is surgically inserted in the patient's pelvis and provides the connection between the tracking device 10 and the patient. Different attachment orientations between the tracking device 10 and the pin are possible, provided the orientation is known and calibrated to match the computer software.

The reference pin may be placed in the pelvis prior to taking x-rays or other imaging of the patient. The position and orientation of the reference pin in the patient's hip is used for the tracking device 10 to locate the surgical tools. Special x-ray markers (like those used in Gunay, M. Three-dimensional bone geometry reconstruction from x-ray images using hierarchical free-form deformation and non-linear optimization [dissertation].Pittsburgh (Pa.): Carnegie Mellon University; 2003.) can be employed to determine the x-ray machine orientation. The pin can then be located in the model through triangulation with two x-ray images from known orientations. In other embodiments, the images of the patient's anatomy may be created through the use of the present invention, such as will be described in more detail hereinbelow.

The display 44 shows one or more images. For example, the display 44 may include a real-time image and the display 44 may include one or more computer generated images according to the present invention. For example, the display 44 may show an actual or a computer generated image of a "target object" and the display 44 may show an image indicative of the spatial position of the working end 18 of the device relative to the target object. The target object may be any object being used with the present invention. For example, in robot teaching applications, the target object may be a workspace in which a robot operates and the display 44 may show a computer generated image of the robot's motion and configuration in response to the motion and configuration of the tracking device 10. In medical applications the target object may be a portion of the patient's anatomy, such as a hip joint, and the working end 18 of the device may be a medical device, such as a scalpel. In that example, the display 44 may show a computer generated image of the medical device relative to the hip joint. The display 44 may include real images, such as from a camera, from an arthroscope inside a patient, or from other imaging devices. In other embodiments, the display 44 may include one or more computer generated images, such as a computer generated image of a hip joint, computer generated images of a medical device located inside the patient or a computer generated image of robot and a corresponding workspace for the robot. In some medical embodiments, the image of the target object is created from conventional medical procedures, such as three-dimensional data obtained from computerized tomography, magnetic resonance imaging, or a recently developed method using x-ray images to create the patient specific model (See, for example, Gunay, M. Three-dimensional bone geometry reconstruction from x-ray images using hierarchical free-form deformation and non-linear optimization [dissertation].Pittsburgh (Pa.): Carnegie Mellon University; 2003.).

The display 44 may be created prior to surgery, or the display 44 may be created during the medical procedure. For example, as will be described in more detail hereinbelow, a three-dimensional image may be created with a sonogram device at the time of the medical procedure. In other embodiments, an arthroscope or other imaging device may be inserted into the body and the images from that device may be used to create two or three-dimensional images as the medical procedure is being performed.

Given the operative tool positions from the tracking device 10, a real-time display 44 of the surgical instruments relative to the patient anatomy can be generated. Traditional arthroscopic surgery limits the surgeon's view to only the camera image of the joint. The present invention allows for the use of additional screens of computer images providing supplementary real-time information about the anatomy surrounding the surgical tools. Other information may also be provided through the present invention, such as monitoring the location of medical devices within the patient and providing a warning if a tools moves into a region that may harm the patient. Additional visual information is especially valuable since most surgeons rely predominantly on visual feedback during surgery (See, for example, Taylor R H. Medical Robotics in Computer-Integrated Surgery. IEEE Transactions on Robotics and Automation. 2003; 19(5):765-81.).

Many variations of the present invention are possible. For example, in other embodiments the reference pin 16 may be attached to a part of the patient other than the pelvis, or attached to a location other than the patient. In addition, although the present invention will often be described in terms of a reference pin 16, the present invention may also be used with the tracking device 10 attached to a reference point other than a reference pin 16. For example, the reference end 14 of the tracking device 10 may be attached to a predetermined location on a table on which the patient is located. In other embodiments, the tracking device 10 may not use a reference pin 16 or any analogous device. For example, the reference end 14 of the device may include a transmitter and one or more receivers in the area may be used to accurately determine the location of the reference end 14. In another example, multiple receivers may be used to triangulate the location of the reference end 14. In other embodiments, the reference end 14 may not include an active transmitter, but may include a passive device, such as a radio frequency identification tag. For example, X-rays, MRI, and CT images may be used to find the location of the reference end 14 of the tracking device 10. Other variations for locating the reference end 14 are also possible.

Figure 10:
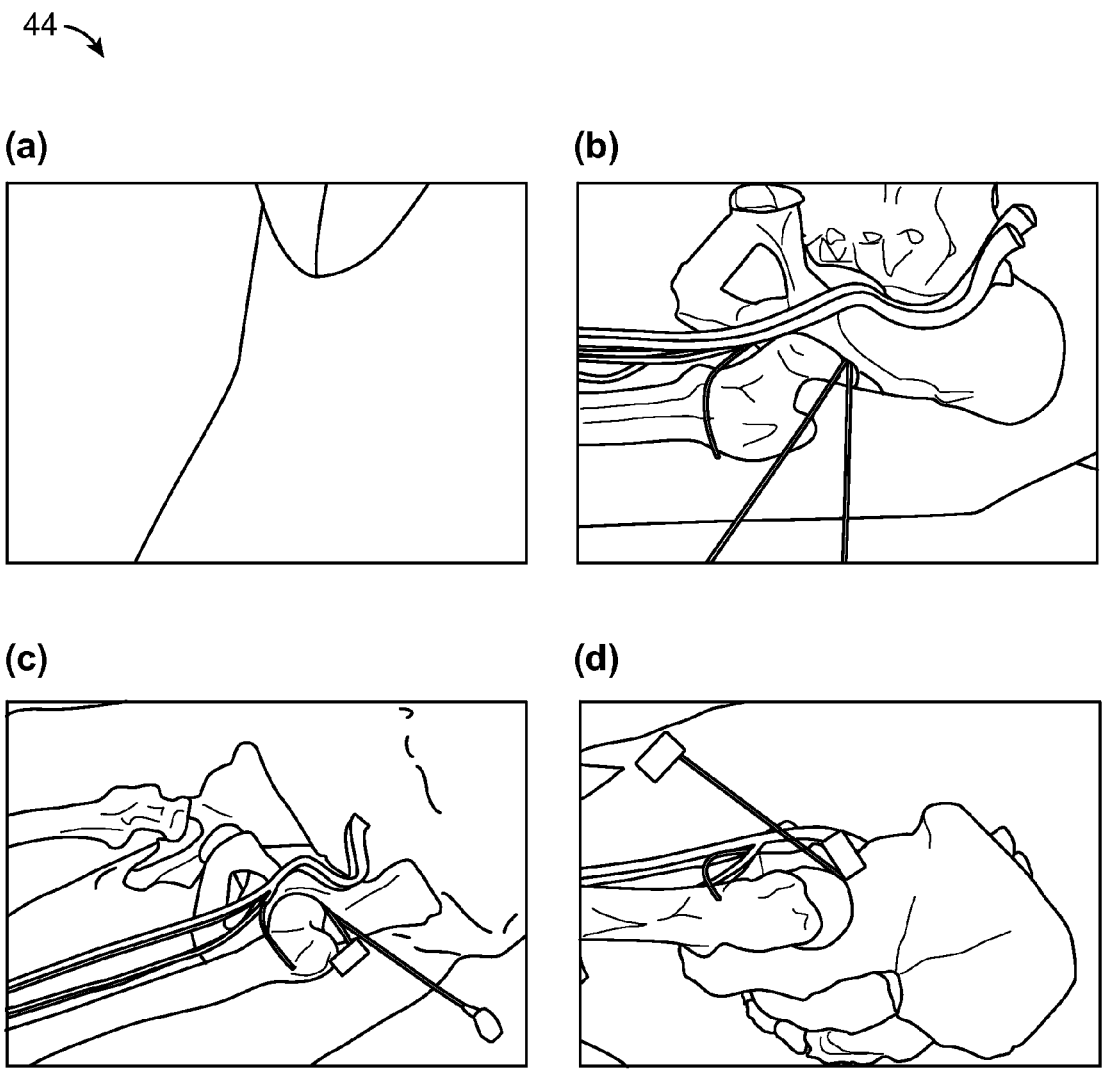
FIGS. 10a-10d illustrate one embodiment of a computer screen display used in accordance with the present invention.

FIG. 10 illustrates one embodiment of a display 44 used in accordance with the present invention. The display 44 shown in FIG. 10 consists of four windows that display different views of the hip joint and surgical tool models. Narrow cylinders, with rounded ends and rectangular handles, are used to represent the arthroscope and a surgical tool. The upper left window, FIG. 10(*a*), displays a picture of the model as viewed from the simulated arthroscope. This window mimics the actual camera image currently used by the surgeon. The remaining three windows, FIGS. 10(*b*)-(*d*), show the model from different perspectives as set by the surgeon. Depending on the specific procedure, the optimal view to observe patient anatomy can be selected. The number of windows used with the present invention may be more or less than four.

As the encoder angles change, the screen images are updated to reflect the new instrument position. The screen display update rate is limited by the speed at which the new transformation matrix can be calculated and the graphics can be redrawn. In one embodiment, the present invention can be implemented on a computer with a 2.2 MHz AMD64 processor, 1.0 GB RAM and a NVIDIA GeForce 6800 GT video card. With this computer, the screen updates approximately every 78 ms or almost 13 frames per second. Different computers and refresh rates may also be used with the present invention.

Figure 11:
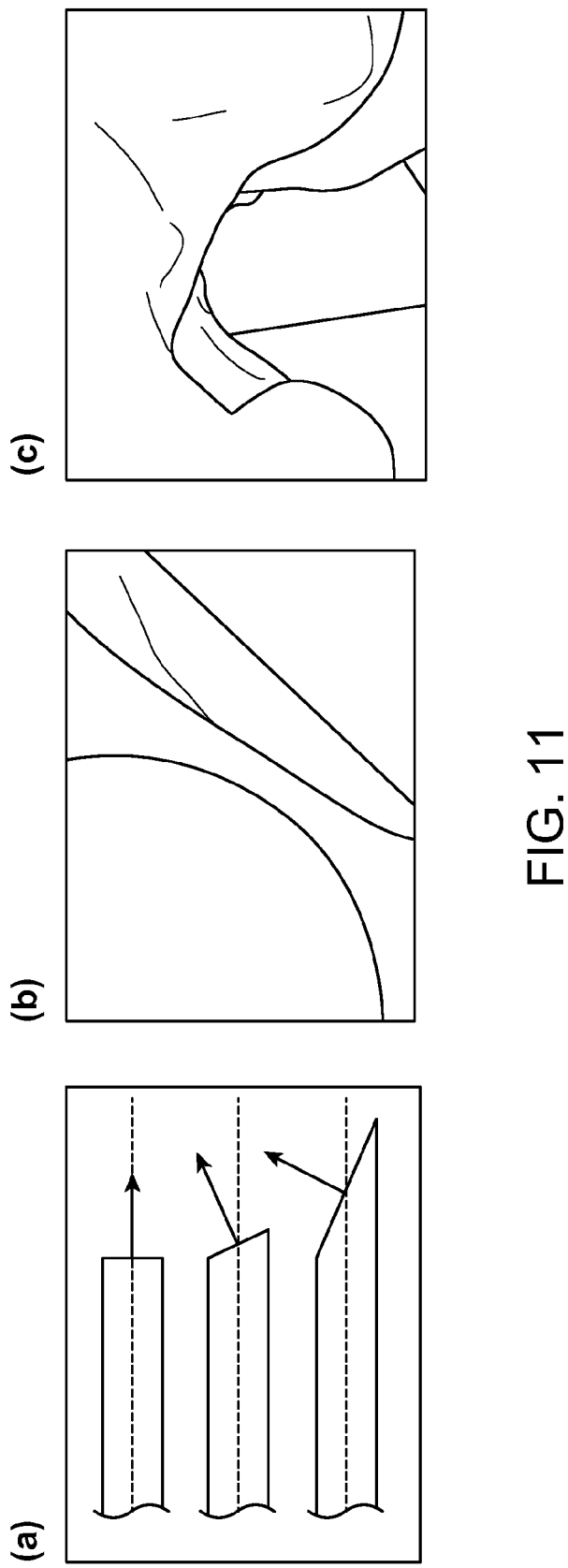
FIGS. 11a-11c illustrate a comparison of arthroscopes with varying viewing angles. The camera angle describes the camera viewing direction. The angle is measured from the axial direction of the tool to the viewing direction.

FIG. 11 illustrates a comparison of arthroscopes with varying viewing angles. The view from an arthroscopic camera is often difficult to interpret because the camera does not look directly in the axial direction, but at an angle to the axial direction. Standard viewing angles are 30° and 70° as shown in FIG. 11(*a*). A 70° viewing angle is more common. There is a significant difference between a 0° and 70° viewing angle as demonstrated by FIGS. 11(*b*) and (*c*). Both images were captured with the tool in the same position and orientation, but with different viewing angles. Since it is often more intuitive to navigate with a 0° viewing angle, the arthroscope view on the computer display 44 can be toggled between the actual arthroscope viewing angle of 70° and the axial direction. The present invention may also be used to provide different angles, such as to cater to the particular needs of the procedure and the preferences of the doctor.

The present invention also allows for new safety features. For example, during portal placement, there is concern about harming the patient's critical neurovascular structures. Thus, some of these structures such as the femoral artery, femoral vein, and ascending branch of the lateral circumflex artery are incorporated into our computer model. To reduce the risk of injury to these structures during portal placement and other surgical maneuvers, the present invention allows for visual feedback to warn the surgeon when tools move too close to the femoral artery and vein, or the sciatic nerve, or to any other area which it to be avoided. In particular, the present invention allows for the designation of unsafe regions and/or safe regions.

Figure 12:
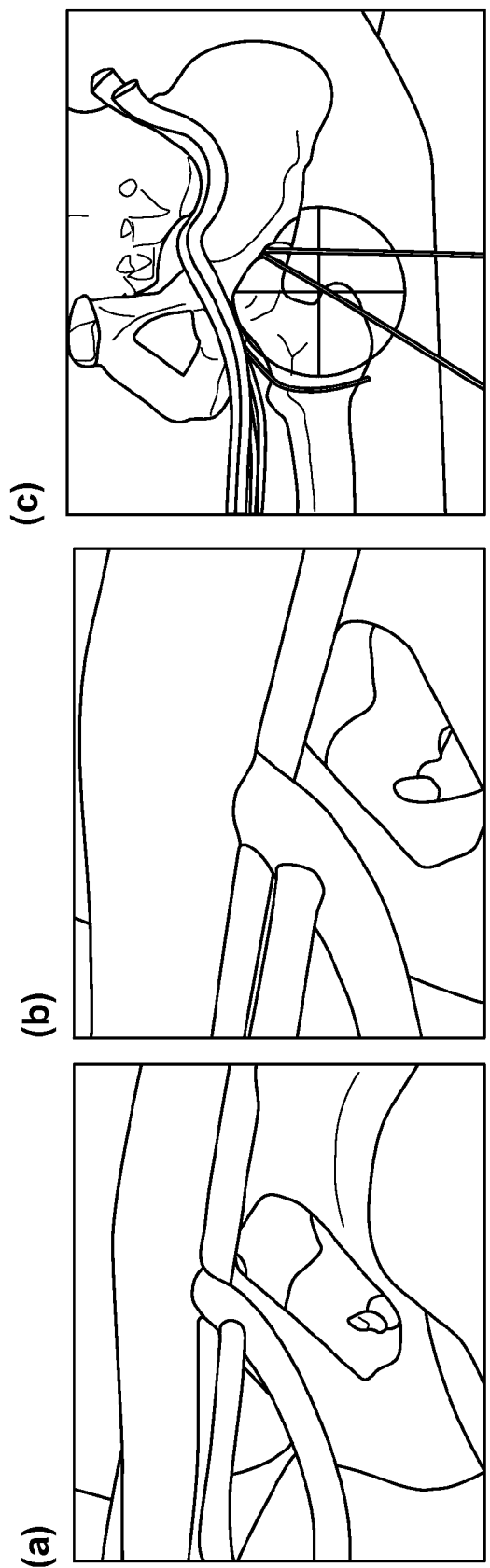
FIGS. 12a-12c illustrate a proximity warning system according to one embodiment of the present invention. As the arthroscope moves outside of the spherically defined safe region and toward the femoral artery, the screen background changes to red to warn the surgeon.

FIG. 12 illustrates a proximity warning system according to one embodiment of the present invention. As the arthroscope moves outside of the spherically defined safe region and toward the femoral artery, the screen background changes to red to warn the surgeon. Other warnings may also be used, such as audible warnings. FIG. 12a illustrates a sphere representing a safe area for tool operation. FIG. 12b illustrates an arthroscopic view from within the safe sphere. FIG. 12c illustrates an arthroscopic view from outside of the safe sphere. An "unsafe region" was defined for the arthroscope and other tools. The arteries and veins are located inside this region. Because these neurovascular structures will shift some amount during the operation, the unsafe region is not defined as the exact geometry of the structures, but as a larger volume which encompasses them. If the surgical instruments move close to the vascular structures and depart from the defined safe region, the screen background changes from white to red as a warning. The surgeon can select the areas to avoid for an optimal surgical result.

The warning system of the present invention is not limited to medical applications. For example, the warning system may be used in robot teaching or in any application in which there are rules regarding the orientation or position of the tracking device 10 or any device with which the tracking device 10 is being used. For example, in robot training there may be limitations on where the robot may be positioned. For example, the robot's motions may be constrained by obstructions like walls, or for safety concerns, such as when people are working nearby, or by other considerations, such as other machines. In addition, the configuration of the robot may be limited. For example, the middle portion of the robot may need to be configured in certain ways in order to operate properly and to avoid people, walls, and other obstacles. In other applications, the tracking device 10 may have a smaller bend radius than the robot, and the warning device is used to alert the user if there is an unacceptable configuration of the tracking device 10, such as one that cannot be assumed by the robot.

In some embodiments, the processor 46 illustrated in FIG. 8 monitors the tracking device 10 and determines if a warning should be generated. For example, the processor 46 may receive signals indicative of a configuration of the tracking device 10, generate instructions for corresponding movements of a robot, determine if the instructions for corresponding movements of the robot violate predetermined rule, and generate a warning signal if the instructions for corresponding movements of the robot violate a predetermined rule. The warning may be audible, visual, or otherwise. The rules may be stored, for example, in the memory 48.

Figure 13:
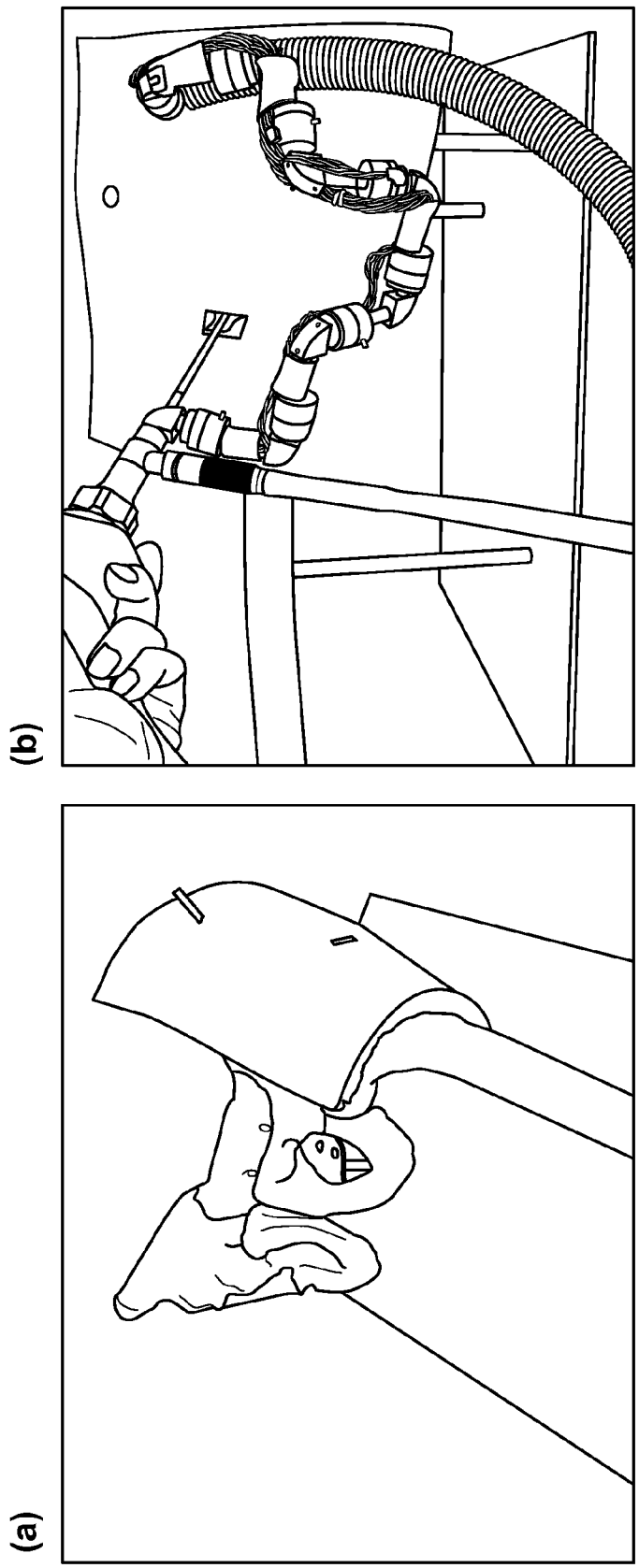
FIGS. 13a and 13b illustrate a hip model and arthroscope connections. The arthroscope must be connected to both the tracking device and traditional arthroscopic equipment (camera head and light source).

FIG. 13 illustrates a hip model and one embodiment of arthroscope connections. To integrate the navigation system of the present invention with existing arthroscopy equipment, a mockup of the human hip joint was created. The model in FIG. 13(a) consists of a mounted femur, pelvis and a foam skin covering. A pin was placed in the pelvis as the reference or base for the tracking device 10. A small hole in the skin model acts as the portal incision.

In one embodiment of the present invention, the computer-aided navigation system is integrated with commercial arthroscopic equipment. This embodiment may include a Sony video monitor, a 4 mm, 70° Video Arthroscope, a Dyonics Xenon light source for the arthroscope, and a Dyonics Vision 325Z Camera System. The video monitor displays the arthroscopic camera images. In FIG. 13(b), the arthroscope is connected to the light source by a fiber optic cable, and to the vision system via the camera head. With the addition of the navigation system, the arthroscope also has a connection to the tracking device 10.

Figure 14:
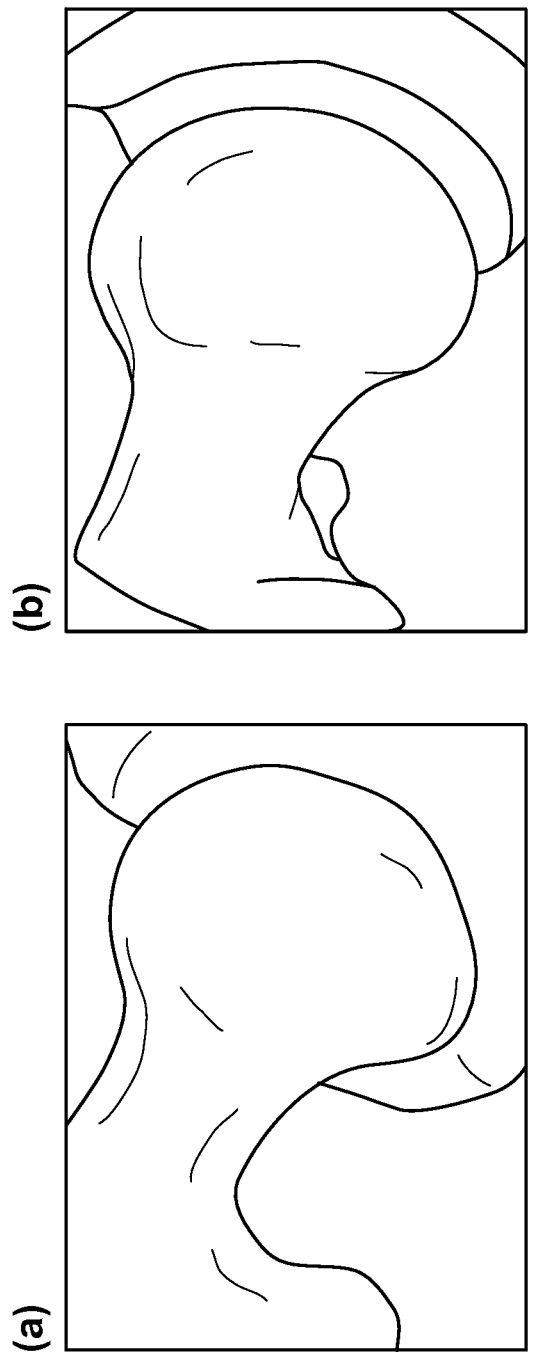
FIGS. 14a and 14b illustrate a comparison of arthroscope views from computer generated display and the actual arthroscope.

When integrating both systems, a comparison of the camera and computer images can be made. The computer image in the upper left window (FIG. 10(a)) should match the image displayed on the video monitor from the arthroscope. Using both the computer navigation system and arthroscopy equipment on the hip model, simultaneous images were collected from the computer screen and the video monitor. FIG. 14 displays an example of the resulting comparison of arthroscope views from computer generated display and an actual arthroscope. It should be noted that the arthroscopic image presented in this example is a much clearer image than typically obtained during surgery. Surrounding body structures prevent the surgeon from obtaining this wide, clear view.

Figure 15A:
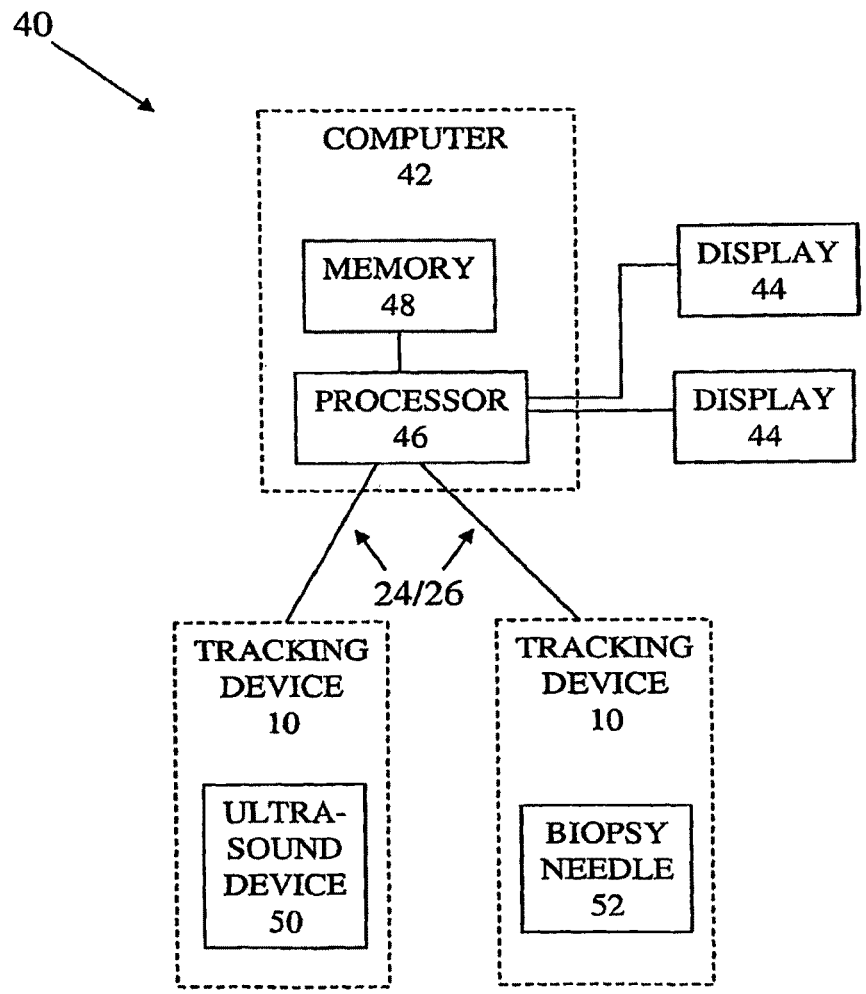
FIGS. 15a and 15b illustrate additional embodiments of the present invention in the form of an ultrasound image-guided biopsy system with three dimensional position sensing and visualization.

FIG. 15a illustrates another embodiment of the present invention in the form of an ultrasound image-guided biopsy system 40 with three dimensional position sensing and visualization. In that embodiment, a tracking device 10 is attached to an ultrasound device 50. The tracking device 10 allows the position and orientation of the ultrasound device 50 to be accurately determined. According to one embodiment of the present invention, the information from the ultrasound device 50 is used along with the position and orientation information from the tracking device 10 to create a three-dimensional image. For example, the ultrasound device 50 may be scanned several times over the area of interest. The images from the ultrasound are then combined with the position and orientation information from the tracking device 10 to create a computer generated three-dimensional image of the area of interest. One or more displays 44 may be used to show the images from the ultrasound device 50 and the computer generated model being created with the data from the ultrasound device 50.

According to another embodiment of the present invention, two devices connected to two different tracking devices 10 are used simultaneously. For example, an ultrasound device 50 may be used in conjunction with one tracking device 10, and a second device (such as a biopsy needle 52) is connected to a second tracking device 10. The information from the ultrasound device and the first tracking device 10 can be used to create a two or three dimensional image shown on one of the displays. The second device (e.g., biopsy needle 52) and second tracking device 10 are used to produce a computer generated image of the second device in the two or three dimensional computer-generated image. As a result, the user can view an image of the area of interest with a computer-generated image of the second device (e.g., a biopsy needle 52) accurately placed in the image. As a result, procedures such as biopsies, which require great skill and/or trial and error to locate the desired target within the body, can be performed by less experienced people with the aid of an accurate, computer-generated image of the target area and the biopsy needle 52. In the illustrated embodiment, two displays 44 are used. The second display may be used, for example, to show the data from the ultrasound device 50 in real time or for other purposes. Although this embodiment is described in terms of an ultrasound device 50 and a biopsy needle 52, other devices, both medical and non-medical, may be used with this and similar embodiments of the present invention.

Many variations of the present invention are possible. For example, rather than using the ultrasound device for medical applications, it may be used for other applications. In some embodiments, an ultrasound device, camera, radar, sonar, or other imaging device is used to create images or models for medical or non-medical applications. For example, an imaging device may be used to create models of objects that are hard to reach or observe by, for example, inserting the imaging device inside the object and scanning the interior while the tracking device 10 correlates the scanned images with precise position and orientation coordinates. In other embodiments, a shape may be imaged by touching a surface with a tool while the tracking device 10 records the particular data points in three dimensional space. In other embodiments, a tool may be moved along a surface while the tracking device 10 records the movement and translates the data into a corresponding computer generated surface. Those and other variations are possible with the present invention.

Applications of the present invention, and any mechanical device, inevitable include errors. For example, the images obtained from the arthroscopic camera and the computer program in FIG. 14 are very similar, but do not match exactly due to several sources of error. One main source of error is the encoders 22 finite resolution. The small errors associated with each encoder's resolution will accumulate to decrease the overall tracking device 10 accuracy. A second source of error results from the initialization method for the tracking device 10. If the tracking device 10 is not positioned precisely during initialization, the calculated transformation matrix for the tracking device 10 will produce inaccurate position values.

Figure 15B:
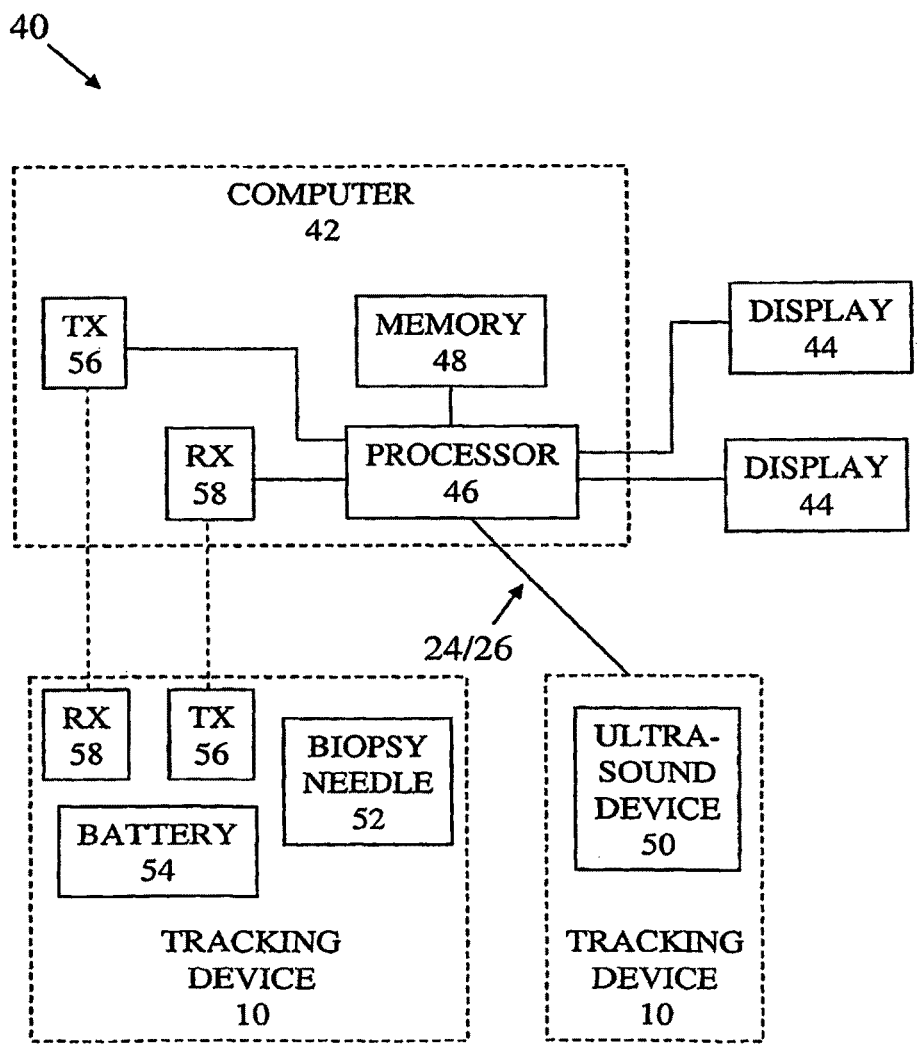

FIG. 15b illustrates another embodiment of the system illustrated in FIG. 15a. In that embodiment, one of the tracking devices 10 includes a battery 54, a wireless transmitter 56, and a wireless receiver 58. The computer 42 also includes a wireless transmitter 56 and receiver 58 for communication with the tracking device 10. As a result, the tracking device 10 is not connected to the computer 42 with wires 24, 26. In other embodiments, the tracking device 10 may still be connected to the computer with communications, power, or other wires or cables. For example, the tracking device 10 may include batteries 54 but not a wireless transmitter 56 and receiver 58, so communications wires are used to connect the computer 42 to the tracking device. In other embodiments, the tracking device may include a wireless transmitter 56 and receiver 58, but not a battery 54, so power lines are used to provide power to the tracking device 10. In other embodiments, the tracking device may include batteries 54, but power lines may still be provided, such as for backup power. Many other variations and combinations are possible with the present invention. For example, in FIG. 15b, the tracking device 10 with the biopsy needle includes a battery 54 and wireless transmitter 56 and receiver 58, while the tracking device 10 with the ultrasound device does not. In other embodiments, both tracking devices may include batteries 54, wireless transmitters 56, and wireless receivers 58.

Figure 16:
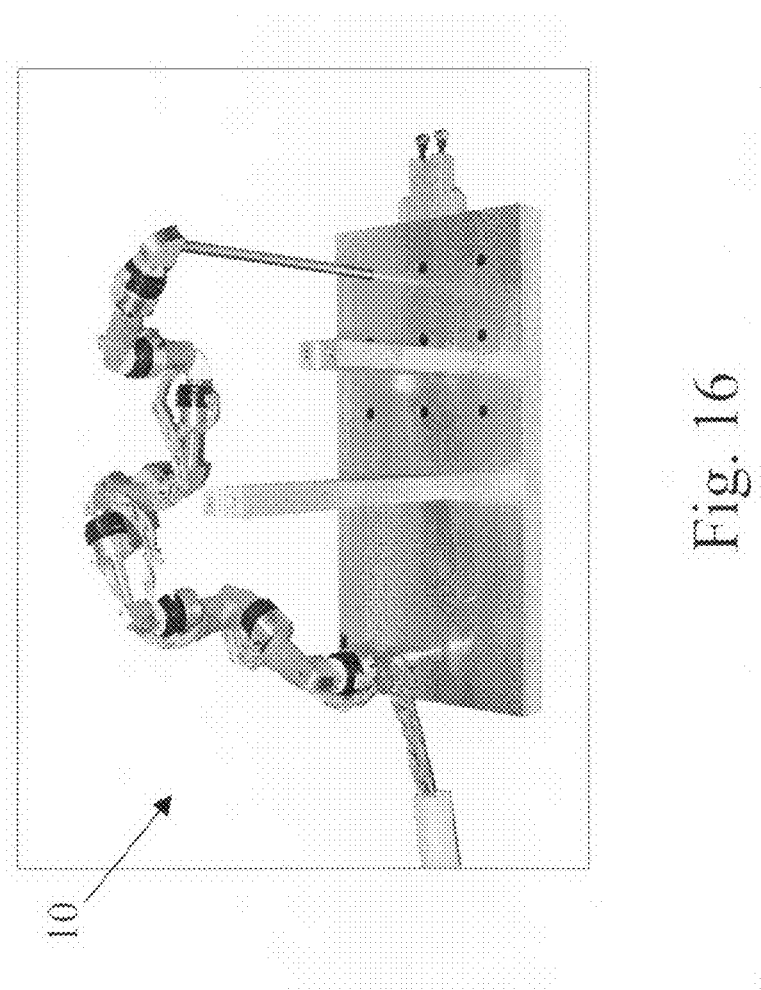
FIG. 16 illustrates another embodiment of an tracking device with a generic tool inserted in one of the machined holes.

FIG. 16 illustrates one embodiment of device used for testing tracking device 10 position error of the present invention. The tracking device 10 position error was tested using the device from the initialization step. The steel rod at the end of the tracking device 10 represents a generic surgical tool, and can be inserted into the grid of machined holes as shown in FIG. 16. The tracking device 10 was initialized as in FIG. 7 and then released to place the tool into a selected hole. The calculated tool position was determined from the encoder measurements and compared to the known location of the machined hole. It is desirable to keep the position error within one millimeter for the overall system (See, for example, Philippon, Marc J., and Fu, Freddie H., 2004, personal communication.).

Two sets of data were collected for analysis. For both cases, ten measurements were taken from four different holes, resulting in forty position measurements. In the first case, the tracking device 10 was initialized between each measurement. The error was determined by calculating the distance between the measured position and the known hole position. This data set considers the absolute error resulting from both the tracking device 10 initialization and encoder readings. In the second test, the tracking device 10 was only initialized once at the start of the forty measurements. In this case, the error was calculated as the distance between the measured position and average position of the measured data. It was found that the second case, in which multiple measurements were averaged together, eliminated significant error from the initialization method.

The first case investigated the tracking devices 10 absolute accuracy, while the second case looked at the tracking devices 10 precision. It was found that the error for the first case was higher than the second case, as listed in Table 1. Given the higher error from the first set of data, the initialization of the tracking device 10 contributes significantly to the 5 mm error in the absolute position. Since the tracking device 10 can be calibrated to eliminate the absolute error and correct the accuracy, the precision data from the second case is of greater interest. The error in the second case is within the 1 mm target. As long as a calibration is performed, the precision data of the second case indicates that the average tracking device 10 error is within the target value.

This work does not address the error resulting from sources such as link 12 length variation from machining and assembly, or wear on the tracking device 10 or attachment mechanisms. A simple method to reduce the error discussed in this application is to select encoders 22 with a higher resolution. In addition, since the encoders 22 can take data at a rate much faster than the rate at which the screen is updated, averaging multiple position measurements may also produce better error results.

TABLE 1

Measured Error Results

|  | Case 1: Multiple Initializations | Case 2: Single Initialization |
|---|---|---|
| Average Error | 5.29 mm | 0.75 mm |
| Standard Deviation | 0.82 mm | 0.55 mm |

Accordingly, another embodiment of the present invention includes improving the accuracy of the present invention by making multiple measurements of the same location. This may be accomplished, for example, by repeatedly moving the tracking device 10 to and from the desired location. In another embodiment, it may be accomplished by maintaining the ends of the tracking device 10 in fixed locations and taking measurements while moving the middle of the tracking device 10. The latter embodiment may be performed by actively moving the middle of the tracking device 10, or it may be accomplished automatically if the nature of the application provides for movement to the middle of the tracking device 10. For example, in a medical application, the tracking device 10 may be moved consistently by the patient's breathing if the tracking device 10 is placed on or near the patient's chest. In other embodiments, one or more links 12 in the device may include actuators, such as electrical or magnetic actuators, to automatically cause movement in the tracking device 10. In other embodiments, the tracking device 10 may include two or more sets of links 12 connecting the working end 18 to the reference end 14, such as illustrated in FIGS. 4a and 4b. In those embodiments, the present invention has at least two paths of links 12 from which to determine the location of the working end 18. The two or more determinations the position of the working end 18 can be averaged or otherwise combined to produce a result with improved accuracy as discussed above.

In other words, the present invention includes a system 40 in which the tracking device 10 includes at least one reference end 14 and first and second paths of series-connected links 12 between the working end 18 and the at least one reference end 14, such as in the embodiment of FIGS. 4a and 4b. The processor 46 determines the spatial position of the working end 18 of the tracking device 10 along the first of the two paths of the series-connected links 12. The processor 46 also determines the spatial position of the working end 18 along the second of the two paths of series-connected links 12. The processor 46 can then average or otherwise combine the data to produce a more accurate result.

The present invention may also be used with more than two paths. For example, the system 40 of the present invention may include a tracking device 10 having more than two paths of series-connected links 12 between the working end 18 and the reference end 14. The processor 46 determines the spatial position of the working end 18 along each of the more than two paths and by averaging or otherwise combining the spatial positions determined along each of the more than two paths. In general, more paths will result in a more accurate determination of the position of the working end 18. In another embodiment, the present invention may be used with two or more paths between the working end 18 and two or more reference ends 14, such as in FIG. 4b. The present invention may also be used with two or more working ends 18 having two or more paths between the working ends 18 and two or more reference ends 14. Other embodiments and variations are also possible.

The present invention can also be used as a tool to address the challenges of joint 20 navigation and portal placement in arthroscopic hip surgery. In the operating room, the system can visually supplement the limiting view from the arthroscope. Specifically, a doctor can view the location of his tools relative to the patient anatomy and be warned when tools enter dangerous regions. This system could also provide an opportunity for medical students to learn and practice the arthroscopic hip procedure.

The following section will discuss some additional variations and alternative embodiments of the present invention in which tracking error can be improved. Tracking accuracy is critical to the success of image-guided systems. Measurement of performance will have no real significance without accurate tracking to provide valid feedback.

One main source of error in mechanical systems, such as those described herein, is in the mechanical design. The present invention was often described in the context of a single bearing connecting one link 12 to the next. Due to the radial clearance in the bearings, there is a small amount of play allowing rotation in the non-axial direction. The small errors associated with each tracking devices 10 non-axial rotation will accumulate to decrease the overall tracking device 10 accuracy. To reduce this problem, an alternative embodiment of the present invention incorporates multiple support bearings. With more than one bearing, the non-axial rotation can be minimized. In addition, tighter tolerances will be provided between adjoining parts.

Figure 17:
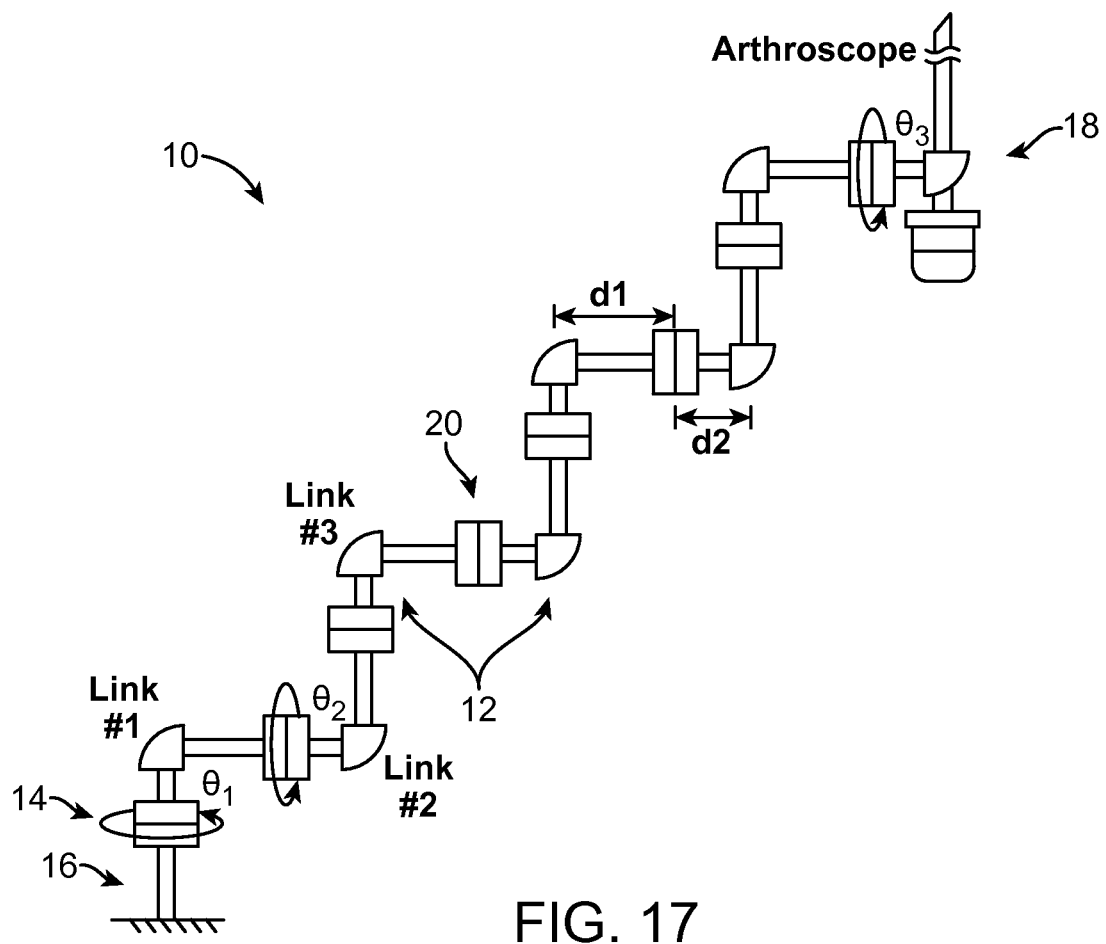
FIG. 17 illustrates another initialization configuration to reduce error. Shown from a top view, the tracking device remains in the horizontal plane.

Another error source is from the encoder initialization method. The initialization is necessary because the encoders 22 selected for the initial prototype are incremental. Each time the tracking device 10 is used, the encoders 22 must be placed in a configuration to set the zero rotation angle to a known position. The initialization embodiment illustrated in FIG. 7 does not provide optimally accurate and consistent placement. For better placement, an alternative embodiment utilizes a horizontal initialization, as show in FIG. 17. If further accuracy is desired, an alternate embodiment uses absolute encoders 22 which do not require an initialization step.

An important source of error results from the encoders 22 finite resolution. The illustrated embodiment was described in terms of encoders 22 that are accurate to approximately 0.3 degrees. In a similar way to the mechanical error, these small discrepancies can accumulate to produce larger tracking errors at the endpoint of the tracking device 10. There are several options to reduce this source of error. A simple method is to utilize encoders 22 with a higher precision. In another embodiment, the present invention uses an averaging technique which utilizes the properties of the redundant tracking device 10.

The averaging technique according to the present invention uses two properties of the tracking device 10: (1) the tracking device 10 is redundant, and (2) the encoders 22 can report data at a much faster rate than the rate at which the screen image is updated. Since the tracking device 10 is redundant and has two extra degrees of freedom, there are an infinite number of tracking device 10 configurations to track any single point. Specifically, when both ends of the tracking device 10 are fixed in a particular position and orientation, the tracking device 10 will still be flexible. This is a result of the extra degrees of freedom; a system with only six degrees of freedom does not have this property. Also, the encoders 22 record a position data point every millisecond while the screen is updated only every 78 milliseconds. Therefore, more data may be accumulated, such as accumulating the 78 points of data for each screen update to produce more accurate position data for the screen display 44.

Figure 18:
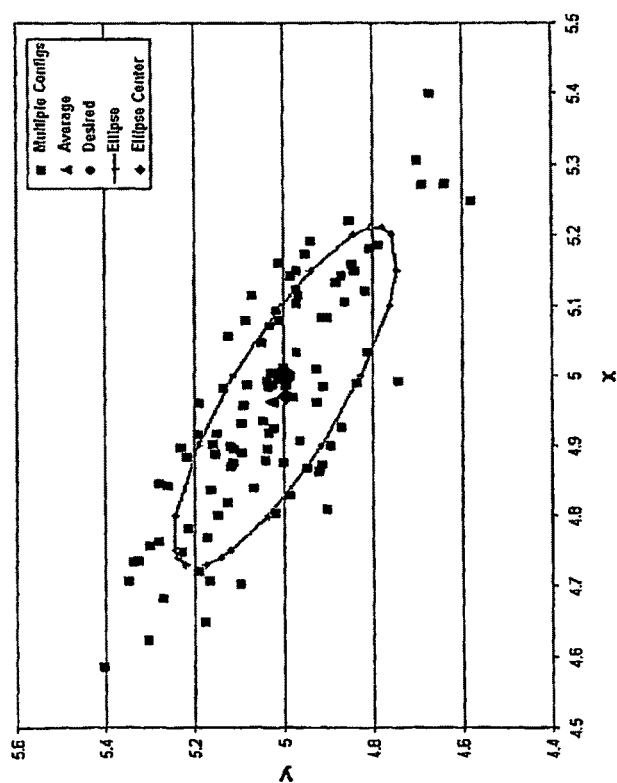
FIG. 18 illustrates test results from multiple configurations of the tracking device around a desired point (circle). The data average (triangle) and the center of a fitted ellipse (diamond) are also shown.

Two possible operations are initially suggested for manipulating the multiple position points. A simple computer program was used to randomly generate error in a sample two-dimensional tracking device 10. The distribution of possible endpoints is shown in FIG. 18, with the large circle as the desired point. A simple, and possibly sufficient, approach is to average the multiple data points and report the average to the screen. The triangle in FIG. 18 is the average of the multiple tracking device 10 configurations. If this technique is not sufficient, using the center of a circle or ellipse fit to the data also may provide better results. The diamond in FIG. 18 is the center of the fitted ellipse.

An important aspect of the present invention is acquiring the patient specific model for the computer display 44. This three-dimensional data can be obtained from computerized tomography, magnetic resonance imaging, or a recently developed method which uses x-ray images to create a patient specific model (See, for example, Gunay M. and K. Shimada, "Three-dimensional bone shape reconstruction from X-ray images using hierarchical free-form deformation and nonlinear optimization," Computer Assisted Radiology and Surgery 2004; and Shim, M., M. Gunay, and K. Shimada, "Three-Dimensional Shape Reconstruction of an Abdominal Aortic Aneurysm form Computer Tomography Images Using Extended Free-Form Deformation," Computer-Aided Design, accepted, 2006.). Also, the position and orientation of the reference pin 16 in the patient's hip must be identified for the tracking device 10 to correctly locate the surgical tools. In some embodiments, the pin will be placed in the pelvis prior to taking x-rays of the patient. Special x-ray markers, like those used in Gunay M. and K. Shimada, "Three-dimensional bone shape reconstruction from X-ray images using hierarchical free-form deformation and nonlinear optimization," Computer Assisted Radiology and Surgery 2004, can be employed to determine the x-ray machine orientation. The pin can then be located in the model through triangulation with two x-ray images from known orientations. For the error reduction described herein, this step is not strictly necessary. However, the addition of this step may be advantageous in some embodiments.

Figure 19:
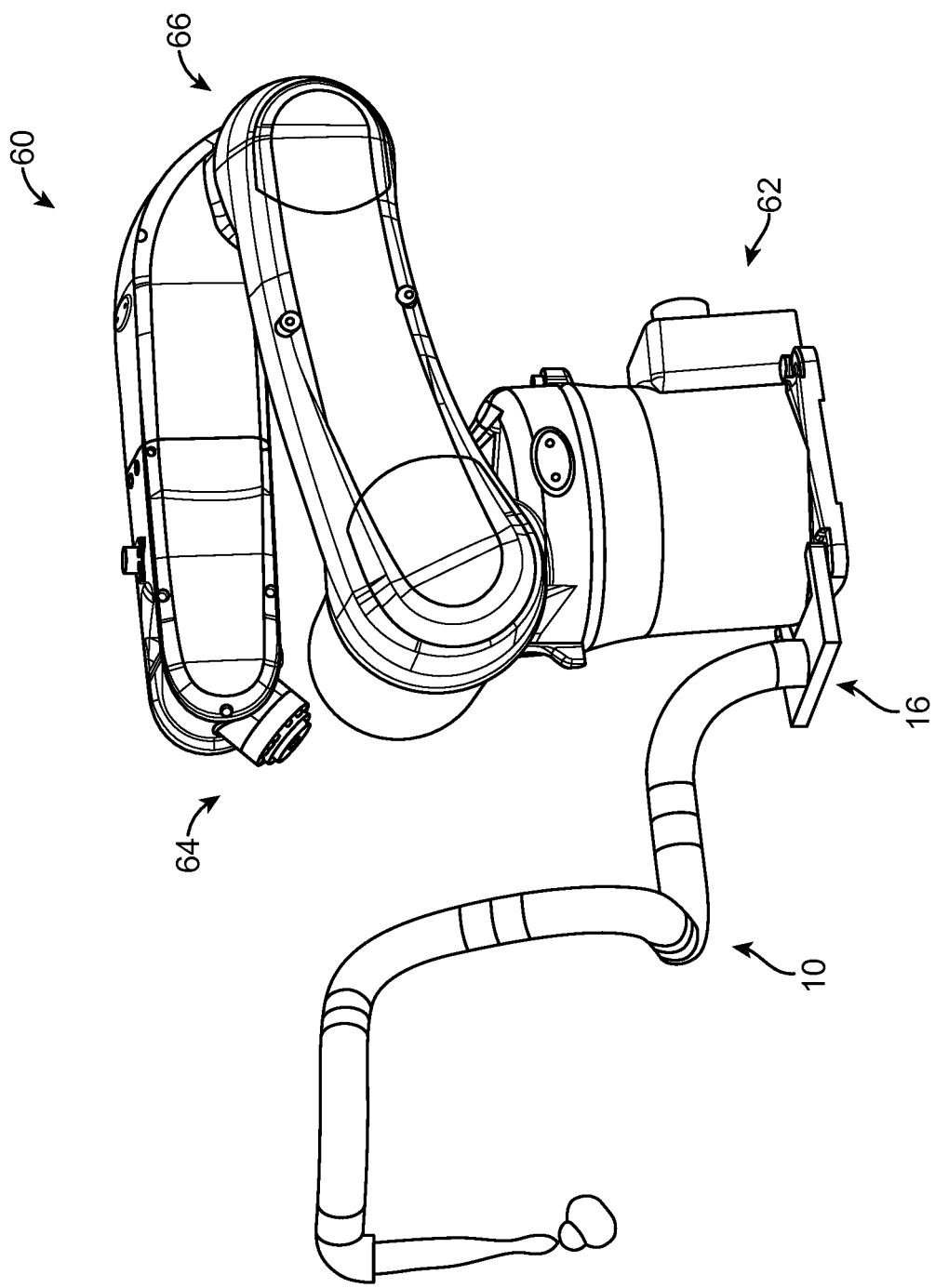
FIGS. 19 and 20 illustrate an embodiment of the present invention used in connection with an industrial robot.

FIG. 19 illustrates another embodiment of the present invention. In that embodiment, the present invention is used to teach a robot 60 how to perform a task and/or for path planning of the robots tasks. In that embodiment, a tracking device 10 according to the present invention is located near the robot 60 with one end anchored at a reference point 16. In the illustrated embodiment, the reference point 16 is at the base of the robot 60, although other reference points may also be used. The tracking device 10 can then be moved to a desired position, such as to retrieve a part. When the tracking device 10 is located in the desired position, the working end or any intermediate part of the tracking device 10 can be determined and that information can be used to program the robot 60 to move to the same position or configuration.

The robot 60 in the illustrated embodiment includes a base 62, an end effecter 64, and a middle portion 66 between the base 62 and the end effecter 64. The robot 60 may also include additional components, as well as more than one recited component. The end effecter 64 may be any end piece for the robot 60, such as for grasping, holding, and releasing objects, for welding, for moving objects, or for any other purpose for which the robot 60 is used.

The present invention may be used with a robot 60 and with a system, such as the system 40 illustrated in FIG. 8, wherein the processor 46 receives signals indicative of movement and configuration of the tracking device 10 and wherein the processor 46 sends signals to the robot 60 indicative of corresponding movement for the robot 60. The present invention may be used to track the working end 18 of the tracking device 10 and provide instructions for corresponding movement to the end effecter 64 and the robot 60. In this way, the present invention may be used to teach robots 60 where and how to move. For example, the present invention may be used to teach robots 60 where to pick up and put down objects.

In other embodiments, particularly those in which the workspace in which the robot 60 operates is constrained, the present invention may be used to allow for teaching a robot 60 how to configure itself when performing tasks. For example, there may be more than one configuration of a robot 60 that allows the end effecter 64 to reach a desired location. The present invention allows a user to configure the tracking device 10 in a desired configuration and for the information regarding the configuration of the tracking device 10 to be used to program or configure the robot 60. For example, the processor 46 according to the present invention receives signals indicative of movement of the tracking device 10 and the processor 46 sends signals to the robot 60 indicative of corresponding movement the robot 60. The movement of the robot 60 may be the movement of the end effecter 64, the movement of the middle portion 66, or the movement of other parts of the robot 60. In another embodiment, the processor 46 receives signals indicative of a configuration of the tracking device 10 and the processor 46 sends signals to the robot 60 indicative of a corresponding configuration of the robot 60. The configuration may be for the middle portion 66 of the robot 60 or for other portions of the robot 60.

Figure 20:
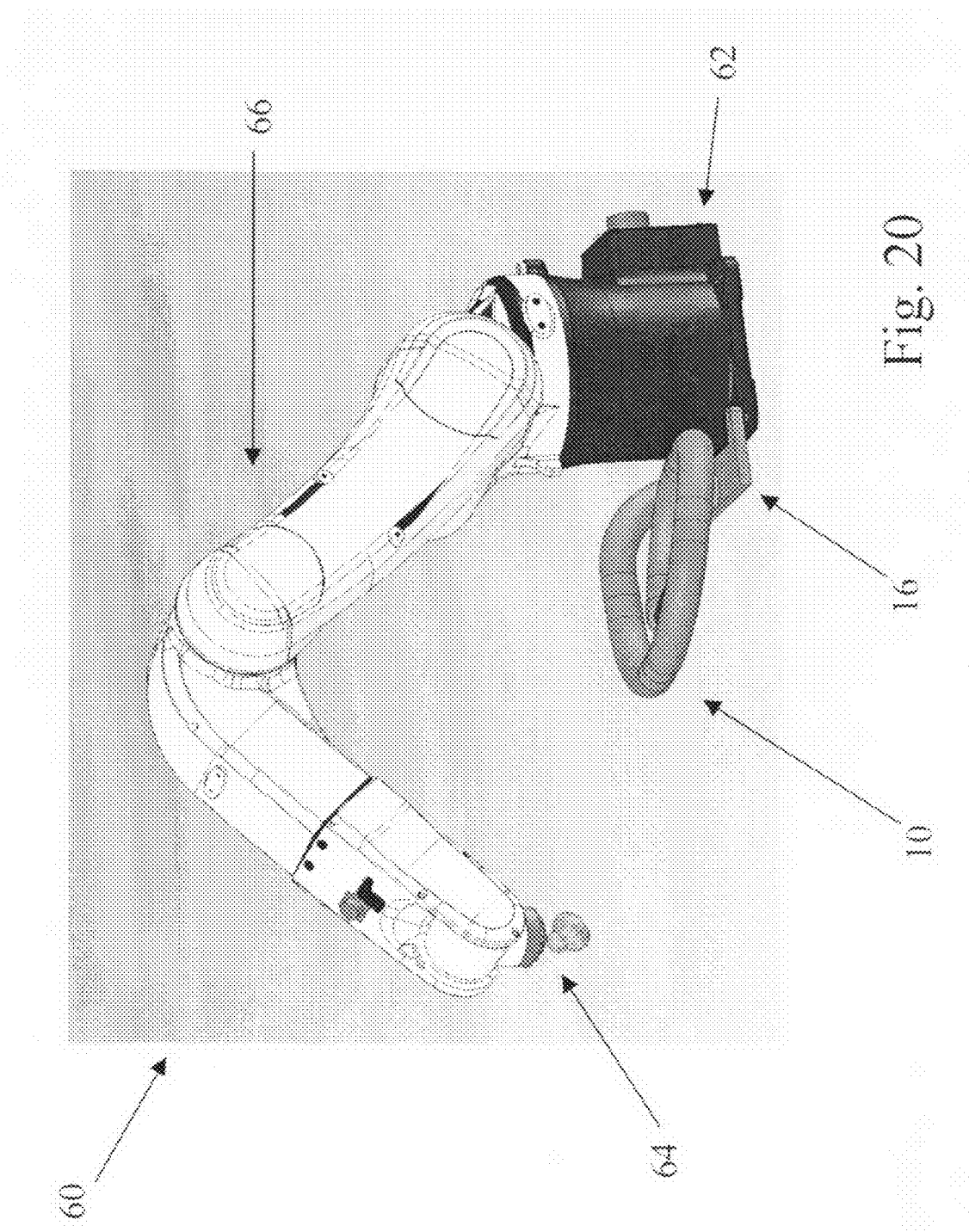

FIG. 20 illustrates the tracking device 10 stored away from the path of the robot 60, and illustrates the robot 60 moving to the desired location and retrieving the part based on the information from the tracking device 10. Prior art robot teaching typically involves the use of a controller through which the movements of the robot 60 are controlled. This process is time consuming and tedious. The present invention allows for a more intuitive and faster approach to teaching robots 60.

Many variations of the tracking device 10 may be used with the present invention. For example, the tracking device 10 may be constructed so that it provides limited resistance to movement. In that embodiment, the device 10 can be moved when desired by a person, but the device holds its shape and position when released. For example, friction fittings may be used in the connections between links 12. Other variations are also possible, such as electromagnets which selectively hold links 12 together when energized and provide no resistance to movement when de-energized.

FIGS. 21-26 illustrate another embodiment of links 12 according to the present invention. In that embodiment, the links 12 are curved pieces with an approximately 90 degree bend. Different bend angles may also be used.

Figure 21:
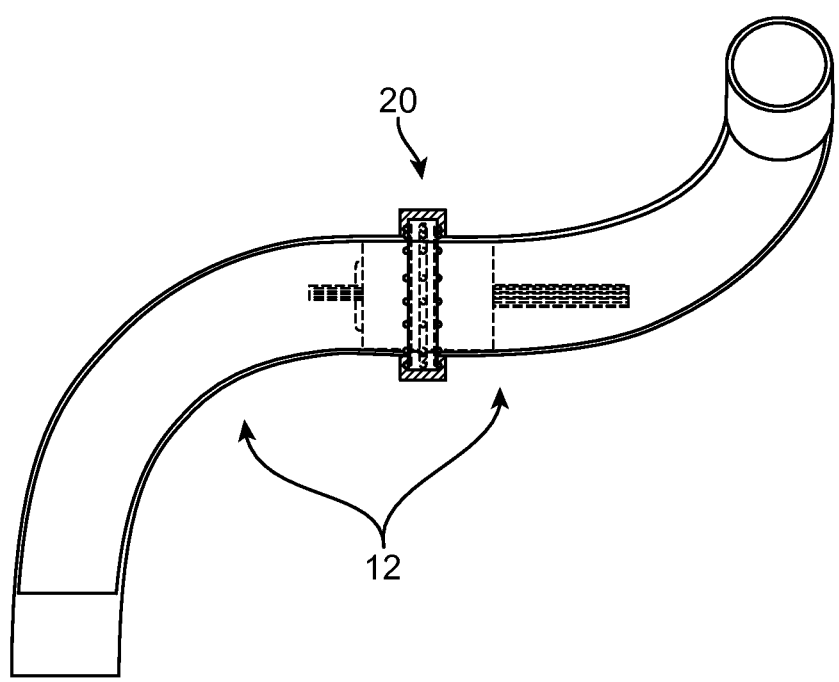
FIG. 21 illustrates another embodiment of adjacent links according to the present invention.
Figure 22:
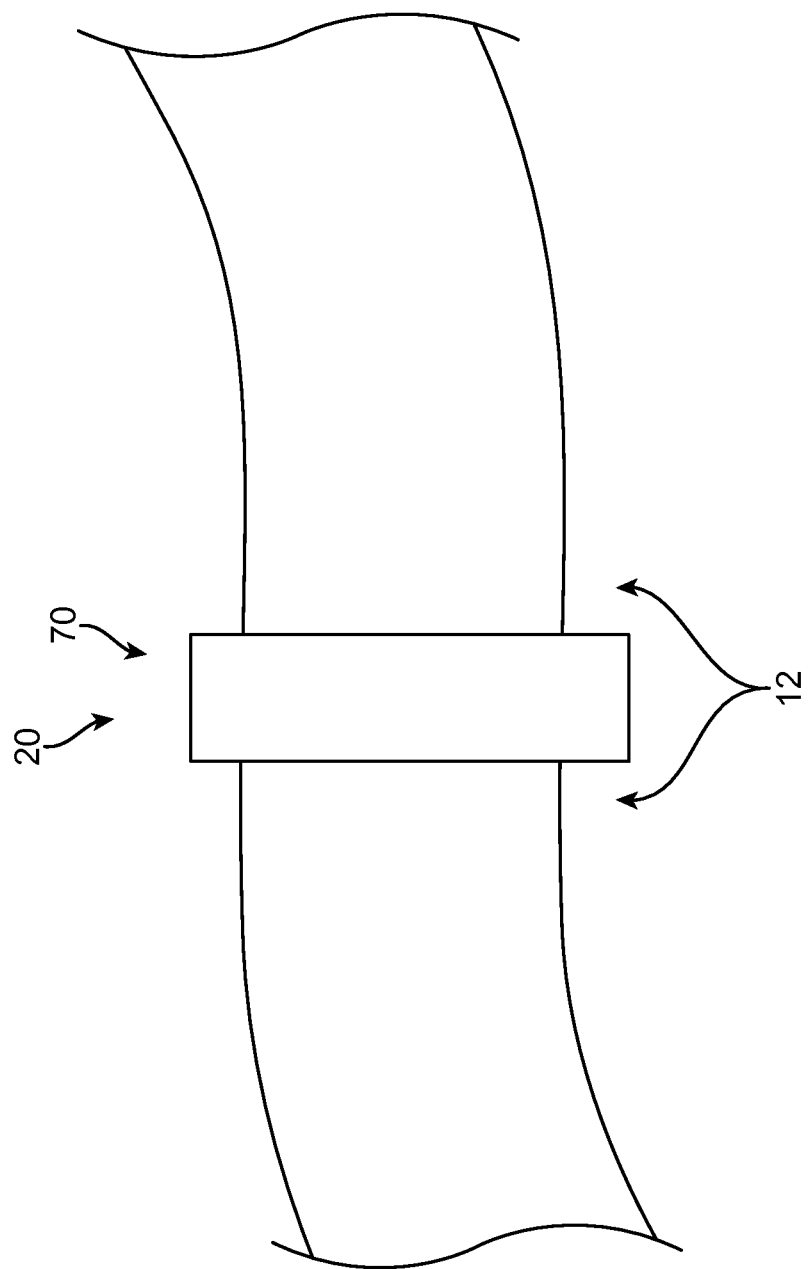
FIG. 22 illustrates the joint design in which an outer ring is used between adjacent links.
Figure 23:
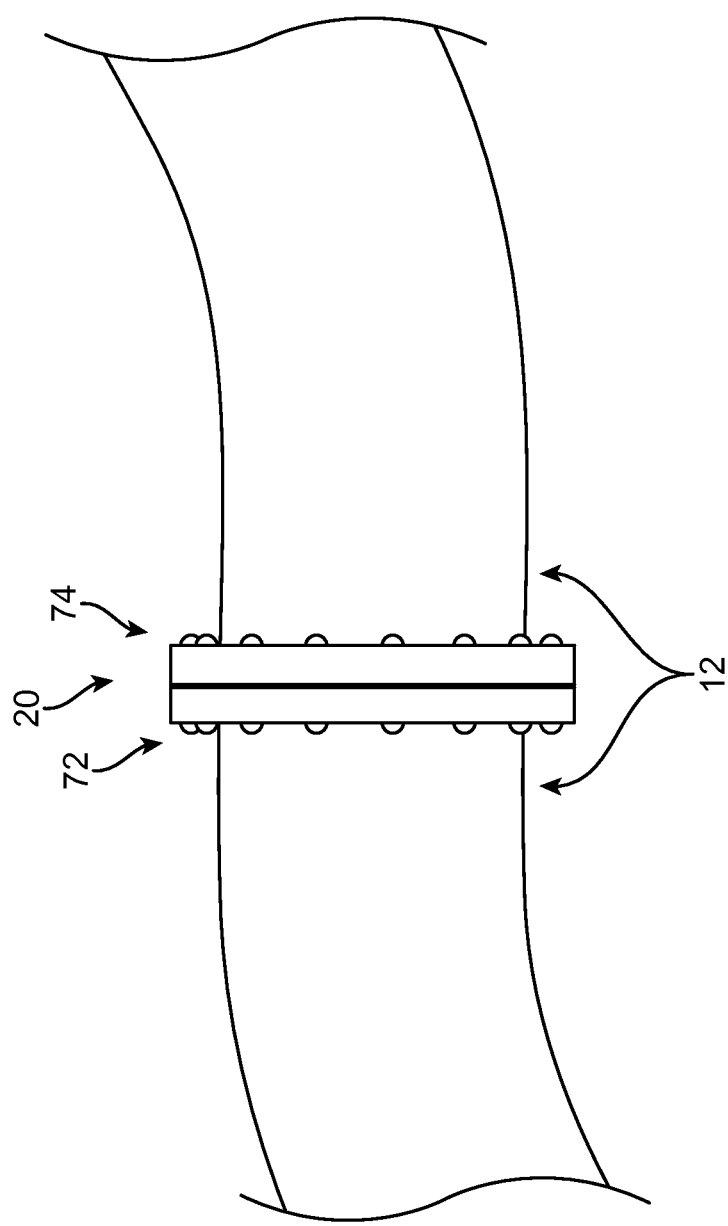
FIG. 23 illustrates left and right connectors in the joint between adjacent links.
Figure 24:
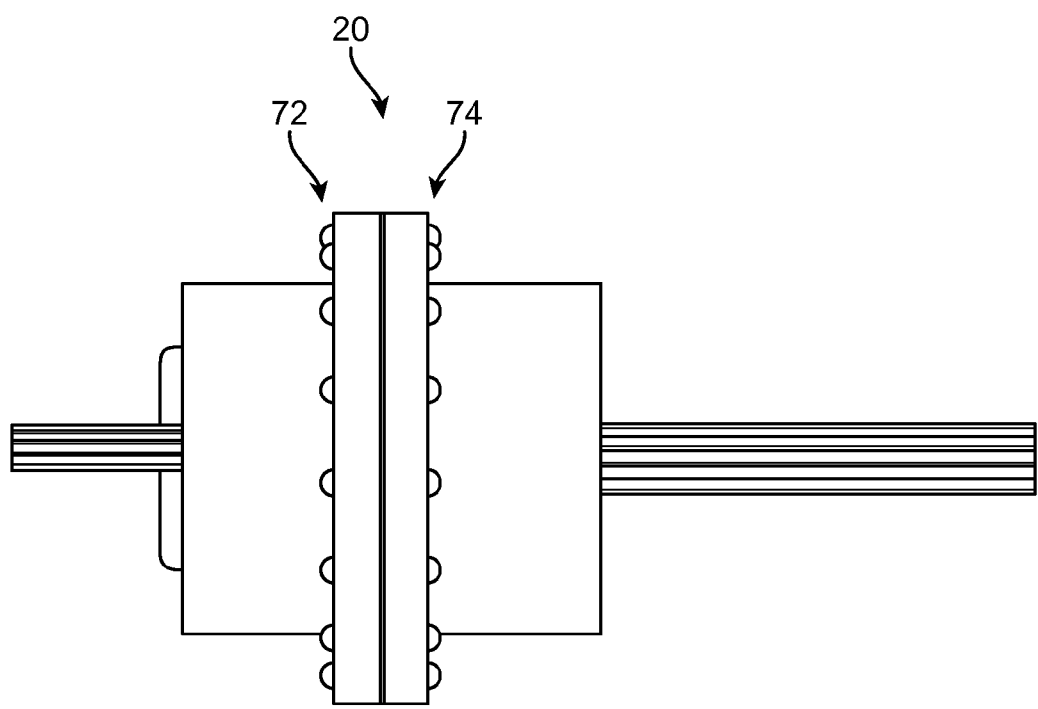
FIG. 24 illustrates a more detailed view of the connector.
Figure 25:
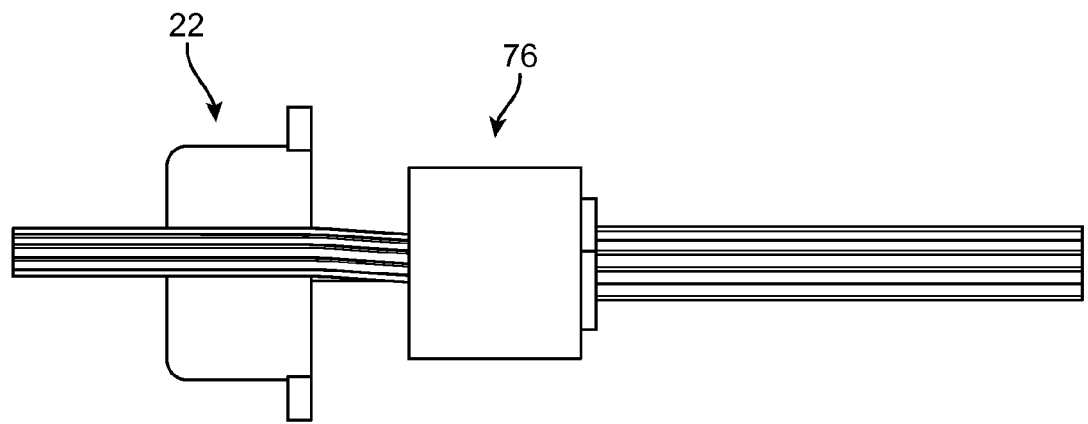
FIG. 25 illustrates a slip ring and an encoder in the connector.
Figure 26:
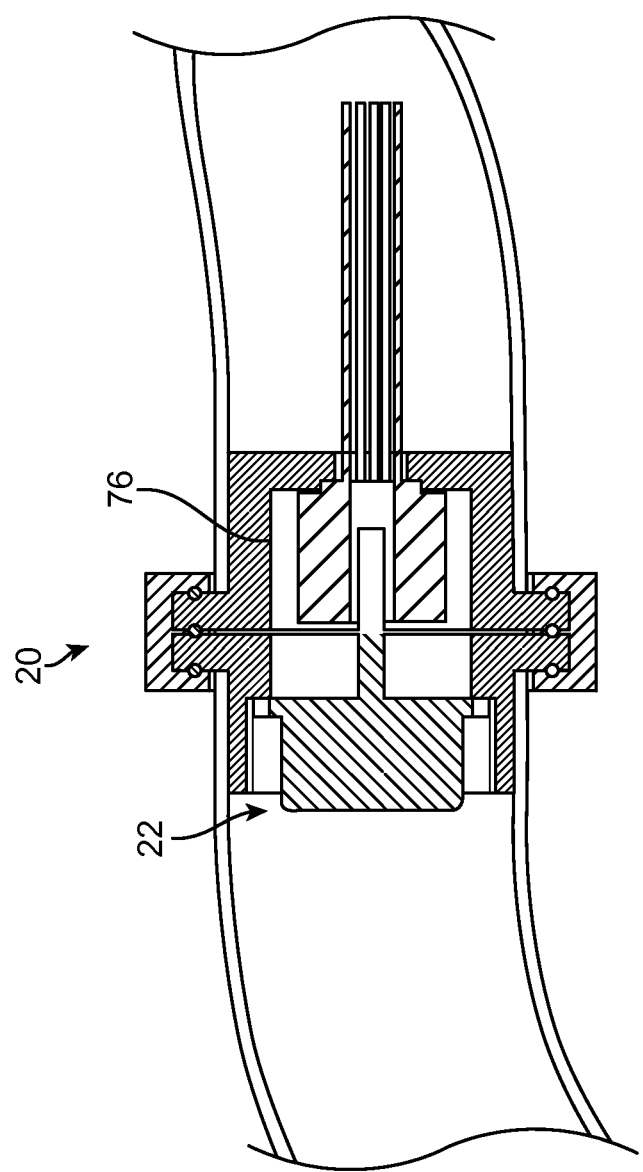
FIG. 26 illustrates a cutaway view of the connection between two adjacent links.

FIG. 21 illustrates two adjacent links 12 connected by a joint 20. FIG. 22 illustrates an embodiment in which an outer ring 70 is used between adjacent links 12. The outer ring 70 may be to protect the joint 20 or for other purposes. FIG. 23 illustrates left 72 and right 74 connectors in the joint 20 between adjacent links 12. FIG. 24 illustrates a more detailed view of the joint 20 with the links 12 removed from the figure. FIG. 25 illustrates a slip ring 76 and an encoder 22 in the joint 20. The slip ring 76 allows for 360 degree motion of the joint 20 without twisting wires, such as power and communications wires discussed above, connected at the joint 20. The encoder 22, as described above, is used to determine the location or movement of one link 12 relative to an adjacent link 12. FIG. 26 illustrates a cutaway view of the joint 20 between two adjacent links 12.

The present invention has been described in the context of "L"-shaped links 12 and "C"-shaped links 12. However, the present invention is not limited to such links 12, and many other embodiments of links 12 are possible with the present invention. FIGS. 27-29 illustrate some other embodiments and variations of links 12 according to the present invention.

FIG. 27 illustrates another embodiment of a link 12 according to the present invention. In that embodiment, two "I"-shaped links 12 are connected together via a pivot point 80. One degree of freedom exists between the links 12 which rotate around a pivot point 80 shared by the links 12.

FIG. 28 illustrates another embodiment of a link 12 according to the present invention. In that embodiment, two degrees of freedom exist between two links 12. One degree of freedom comes from rotation of one link 12 relative to the other. In the illustrated embodiment the links 12 rotate around a common axis. Another degree of freedom comes from one link 12 telescoping relative to the other. The illustrated link 12 may be combined with other types of links 12, such as the link 12 in FIG. 27, for use in embodiments in which more freedom of motion is desired.

FIG. 29 illustrates another embodiment of a link 12 according to the present invention. In that embodiment, three degrees of freedom exist between the links 12. Two degrees of freedom allow for movement front-to-back and side-to-side, and the third degree of freedom comes from rotation of one link 12 relative to the other. This link 12 is analogous to a ball and socket joint 20. Many other embodiments, variations, and combinations of links 12 are possible with the present invention.

Although the present invention has been described in terms of specific embodiments, the present invention has many applications, modifications, and variations. For example, although the present invention has been described in terms of particular dimensions and specifications, the present invention is not limited to those specific dimensions and specifications. In addition, the number of working ends 18, reference ends 14, and middle sections of the tracking devices 10 may be different from those specifically described herein. The number of links 12 in the tracking devices 10 may be different than those specifically described herein. The shape of the links 12 in the tracking device 10 may be different than the shapes specifically described herein. The computers used with the present invention may be different than that specifically described herein. The applications and other components and devices used with the present invention may be different than those specifically described herein. The number of degrees of freedom may vary from those specifically described herein. Those other applications, modifications, and variations of the present invention are possible and contemplated, and it is intended that the foregoing specification and the following claims cover such applications, modifications, and variations.

The invention claimed is

1. A system for determining a spatial position of a tool manipulated within a workspace by a human, comprising:
   a tracking device designed and configured for tracking at least a portion of the tool during manipulation of the tool by the human within the workspace to perform a task, the tracking device including:
      a working end comprising the tool, wherein the working end is grasped and moved by the human during the manipulation and the tracking;
      a reference end spaced from the working end;
      a plurality of links connecting the working end to the reference end, wherein each link has at least one degree of freedom relative to an adjacent link, wherein the plurality of links are joined to one another with movable joints to form at least one link set between the reference end and the working end, the link set designed and configured to allow the plurality of links to move relative to one another as the human grasps and moves the working end during use of the tool to perform the task;
      a plurality of sensors measuring the orientation of the links in a plurality of degrees of freedom as the human grasps and moves the working end during use of the tool to perform the task, wherein X is a minimum number of degrees of freedom about which information is required to define the spatial position; and
      a processor receiving information from the sensors and determining the spatial position of the working end of the tracking device relative to the reference end of the tracking device based on information from the sensors measuring Y degrees of freedom, wherein Y is greater than X.

2. The system of claim 1, wherein the tracking device includes a plurality of working ends, with each working end connected to the reference end via a corresponding set of series-connected links and comprising a corresponding tool, wherein each corresponding set of series-connected links is designed and configured so that when the reference end is located for use of the tracking device with the workspace, the human can directly manipulate the corresponding tool within the workspace.

3. The system of claim 1, wherein the tracking device comprises a plurality of link paths and includes a plurality of reference ends, with each reference end is connected to the working end via the plurality of link paths.

4. The system of claim 1, wherein the tracking device includes:
   a plurality of working ends each comprising a corresponding tool to be directly manipulated within the workspace via grasping of the corresponding tool by the human; and
   a plurality of reference ends, wherein the working ends are connected to the reference ends via a plurality of sets of series-connected links.

5. The system of claim 1, wherein the links include:
   a first set of series-connected links connecting the reference end to the working end; and
   a second set of series-connected links connecting the reference end to the working end, wherein the first set of series connected links includes at least one link that is not in the second set of series-connected links.

6. The system of claim 1, wherein each link can rotate at least 360 degrees relative to an adjacent link.

7. The system of claim 1, wherein the links are connected by joints, and wherein the joints have resistance to motion sufficient for the tracking device to maintain a shape under its own weight.

8. The system of claim 7, wherein the resistance to motion of the joints is adjustable.

9. The system of claim 1, wherein the tool is connected to a link measuring at least one degree of freedom.

10. The system of claim 1, wherein the processor is connected to the tracking device via an electrical connection and wherein the processor receives information from the sensors via electrical signals transmitted on the electrical connection.

11. The system of claim 1, wherein the processor is connected to the tracking device via a wireless connection and wherein the processor receives information from the sensors via signals transmitted via the electrical connection.

12. The system of claim 1, further comprising at least one additional tracking device designed and configured for use in determining a spatial position of at least one corresponding additional tool directly manipulated within the workspace by the human, wherein the at least one additional tracking device includes:
   a working end comprising the at least one corresponding additional tool;
   a reference end;
   a plurality of links connecting the working end to the reference end, wherein each link has at least one degree of freedom relative to an adjacent link, wherein the plurality of links of the at least one additional tracking device are designed and configured so that, when the reference end of the at least one additional tracking device is located for use of the additional tracking device with the workspace, the human can directly manipulate the additional tool within the workspace via grasping of the at least one corresponding additional tool by the user; and
   a plurality of sensors measuring the orientation of the links in a plurality of degrees of freedom, wherein X is a minimum number of degrees of freedom about which information is required to define the spatial position;
   wherein the processor receives information from the sensors in the at least one additional tracking device and wherein the processor determines the spatial position of the working end of the at least one additional tracking device relative to the reference end of the at least one additional tracking device based on information from the sensors measuring Y degrees of freedom, wherein Y is greater than X.

13. The system of claim 1, further comprising a display connected to the processor.

14. The system of claim 13, wherein the processor sends signals to the display which cause the display to produce computer-generated images of real-time motion of the tool in the workspace.

15. The system of claim 13, wherein the processor sends signals to the display which cause the display to show a computer-generated image of a target object within the workspace and an image indicative of the spacial position of the working end relative to the target object.

16. The system of claim 15, wherein the target object is a portion of human anatomy.

17. The system of claim 1, wherein the reference end of the tracking device is connected to a reference pin attached to a human being.

18. The system of claim 1, further comprising:
a second tracking device designed and configured for use in determining an additional spatial position of a second tool directly manipulated within the workspace via grasping by the human, wherein the second tracking device includes:
a working end comprised of the second tool;
a reference end;
a plurality of links connecting the working end to the reference end, wherein each link has at least one degree of freedom relative to an adjacent link, wherein the plurality of links of the second tracking device are designed and configured so that, when the reference end is located for use of the second tracking device with the workspace, the human can directly manipulate the second tool within the workspace; and
a plurality of sensors measuring the orientation of the links in a plurality of degrees of freedom, wherein X is a minimum number of degrees of freedom about which information is required to define the spatial position;
a display connected to the processor;
wherein the processor:
receives information from the sensors in the second tracking device;
determines the spatial position of the working end of the second tracking device relative to the reference end of the second tracking device based on information from the sensors measuring Y degrees of freedom, wherein Y is greater than X;
sends signals to the display which cause the display to produce at least one image of a first tool model as a function of the spatial position of the working end of the tracking device determined by the processor; and
sends signals to the display which cause the display to produce at least one image of a second tool model as a function of the spatial position of the working end of the second tracking device determined by the processor.

19. The system of claim 18, wherein the processor sends signals to the display which cause the display to display, simultaneously:
an image of a target object within the workspace, wherein the image of the target object is a computer-generated image;
the image of the first tool model within the image of the target object; and
the image of the second tool model within the image of the target object.

20. The system of claim 18, wherein:
the tool includes a medical device;
the working end of the second tracking device includes an imaging device; and
the processor sends signals to the display which cause the display to produce at least one image of a model of the medical device indicative of the spatial position of the medical device relative to an image generated by the imaging device.

21. The system of claim 1, further comprising a robot having a base, an end effecter, and a middle portion connecting the base and the end effecter, wherein the processor receives signals indicative of movement of the working end of the tracking device and wherein the processor sends signals to the robot indicative of corresponding movement for the end effecter.

22. The system of claim 1, further comprising a robot having a base, an end effecter, and a middle portion connecting the base and the end effecter, wherein the processor receives signals indicative of movement of the tracking device and wherein the processor sends signals to the robot indicative of corresponding movement for the middle portion of the robot.

23. The system of claim 1, further comprising a robot having a base, an end effecter, and a middle portion connecting the base and the end effecter, wherein the processor receives signals indicative of a configuration of the tracking device and wherein the processor sends signals to the robot indicative of a corresponding configuration for the middle portion of the robot.

24. The system of claim 1, wherein the processor generates a warning signal in response to the tracking device entering into a predetermined spatial region.

25. The system of claim 1, wherein the processor generates a warning signal in response to the tracking device assuming a predetermined configuration.

26. The system of claim 1, wherein the processor:
receives signals indicative of a configuration of the tracking device;
generates instructions for corresponding movements of a robot;
determines if the instructions for corresponding movements of the robot violate predetermined rule; and
generate a warning signal if the instructions for corresponding movements of the robot violate a predetermined rule.

27. The system of claim 1, wherein:
the tracking device includes at least one reference end and first and second paths of series-connected links between the working end and the at least one reference end; and
the processor determines the spatial position of the working end of the tracking device relative to the at least one reference end of the tracking device by:
determining the spatial position of the working end relative to the at least one reference end along the first of the two paths of series-connected links;
determining the spatial position of the working end relative to the at least one reference end along the second of the two paths of series-connected links; and
averaging the spatial positions determined along the first and second paths.

28. The system of claim 27, wherein:
the tracking device includes more than two paths of series-connected links between the working end and the at least one reference end;
and the processor determines the spatial position of the working end of the tracking device relative to the at least one reference end of the tracking device by:
determining the spatial position of the working end relative to the at least one reference end along each of the more than two paths; and
averaging the spatial positions determined along each of the more than two paths.

29. A system for determining a spatial position, comprising:
- a tracking device including:
  - a working end;
  - a reference end;
  - a plurality of links connecting the working end to the reference end, wherein each link has at least one degree of freedom relative to an adjacent link, wherein the plurality of links are joined to one another with movable joints to form a link set between the reference end and the working end, the link set designed and configured to allow the plurality of links to move relative to one another as a human grasps and moves the working end to perform a task;
  - a plurality of sensors measuring the orientation of the plurality of links in a plurality of degrees of freedom as the human grasps and moves the working end to perform the task, wherein X is a minimum number of degrees of freedom about which information is required to define the spatial position; and
  - a processor receiving information from the sensors and determining the spatial position of the working end of the tracking device relative to the reference end of the tracking device based on information from the sensors measuring Y degrees of freedom, wherein Y is greater than X;
- wherein the processor determines the spatial position of the working end of the tracking device relative to the reference end of the tracking device by:
  - determining, a plurality of times, the spatial position of the working end relative to the reference end when the working end and the reference end are stationary relative to one another and when at least one of the links connecting the working end to the reference end is moving so as to generate a plurality of calculated position data points; and
  - averaging the plurality of calculated position data points so as to generate an update data point.

* * * * *